(12) United States Patent
Plaksin et al.

(10) Patent No.: US 10,464,984 B2
(45) Date of Patent: Nov. 5, 2019

(54) OPTIMIZED NUCLEIC ACID SEQUENCES CODING FOR THE ALPHA-CHAIN OF HUMAN CHORIONIC GONADOTROPIN

(71) Applicant: FERRING B.V., Hoofddorp (NL)

(72) Inventors: Daniel Plaksin, Hoofddorp (NL); Ayelet Grinhut, Hoofddorp (NL)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 15/566,961

(22) PCT Filed: Apr. 22, 2016

(86) PCT No.: PCT/EP2016/059006
§ 371 (c)(1),
(2) Date: Oct. 16, 2017

(87) PCT Pub. No.: WO2016/170113
PCT Pub. Date: Oct. 27, 2016

(65) Prior Publication Data
US 2018/0127477 A1    May 10, 2018

(30) Foreign Application Priority Data
Apr. 24, 2015 (EP) .................................... 15164965

(51) Int. Cl.
| C07K 14/59 | (2006.01) |
| C12N 9/10 | (2006.01) |
| A61K 38/16 | (2006.01) |
| C12N 15/63 | (2006.01) |
| A61P 5/06 | (2006.01) |

(52) U.S. Cl.
CPC .............. *C07K 14/59* (2013.01); *A61K 38/16* (2013.01); *A61P 5/06* (2018.01); *C12N 9/1081* (2013.01); *C12N 15/63* (2013.01); *C12Y 204/99004* (2013.01); *C07K 2317/14* (2013.01); *C07K 2317/41* (2013.01); *C12N 2800/22* (2013.01)

(58) Field of Classification Search
None
See application file for complete search history.

(56) References Cited

U.S. PATENT DOCUMENTS 8,326,547 B2 * 12/2012 Liu .................... G06F 19/22
702/19
2003/0036181 A1   2/2003 Okkels et al.
2003/0092160 A1   5/2003 Bout et al.
2013/0023476 A1   1/2013 Cottingham et al.
2013/0259924 A1  10/2013 Bancel et al.

FOREIGN PATENT DOCUMENTS

WO    WO 01/58493      *   8/2001 ............. A61K 47/48
WO    WO-2011/084145 A2    7/2011
WO    WO-2013/151666 A2   10/2013
WO    WO-2011/042688 A1   10/2016

OTHER PUBLICATIONS

Phillips, A., J Pharm Pharmacology, 2001; 53: 1169-1174 (Year: 2001).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Vervoort et al., Nucleic Acids Research, 2000; 28: 2069-2074. (Year: 2000).*
Presnyak et al., Cell, 2015; 160: 1111-1124 (Year: 2015).*
The website downloaded Jun. 26, 2019 from www.gmp-creativebiolabs.com/per-c6-cell-lines_74.htm; three pages total (Year: 2019).*
Sequence 1926 from Patent WO2013151666 (retrieved from EBI accession No. EM_Pat:JC113281, Jan. 28, 2014).
Examination Report dated Mar. 21, 2019 from Chilean Application No. 201702661.
English summary of Colombian Examination Report (summary dated Jun. 4, 2019).

* cited by examiner

*Primary Examiner* — Christina M Borgeest
(74) *Attorney, Agent, or Firm* — Foley & Lardner LLP

(57) ABSTRACT

A host cell characterized in that it comprises integrated into its genome a sequence coding for the a chain of hCG, and use of the host cell to produce recombinant hCG.

17 Claims, 6 Drawing Sheets

Specification includes a Sequence Listing.

Fig 1: Optimised hCG alpha:
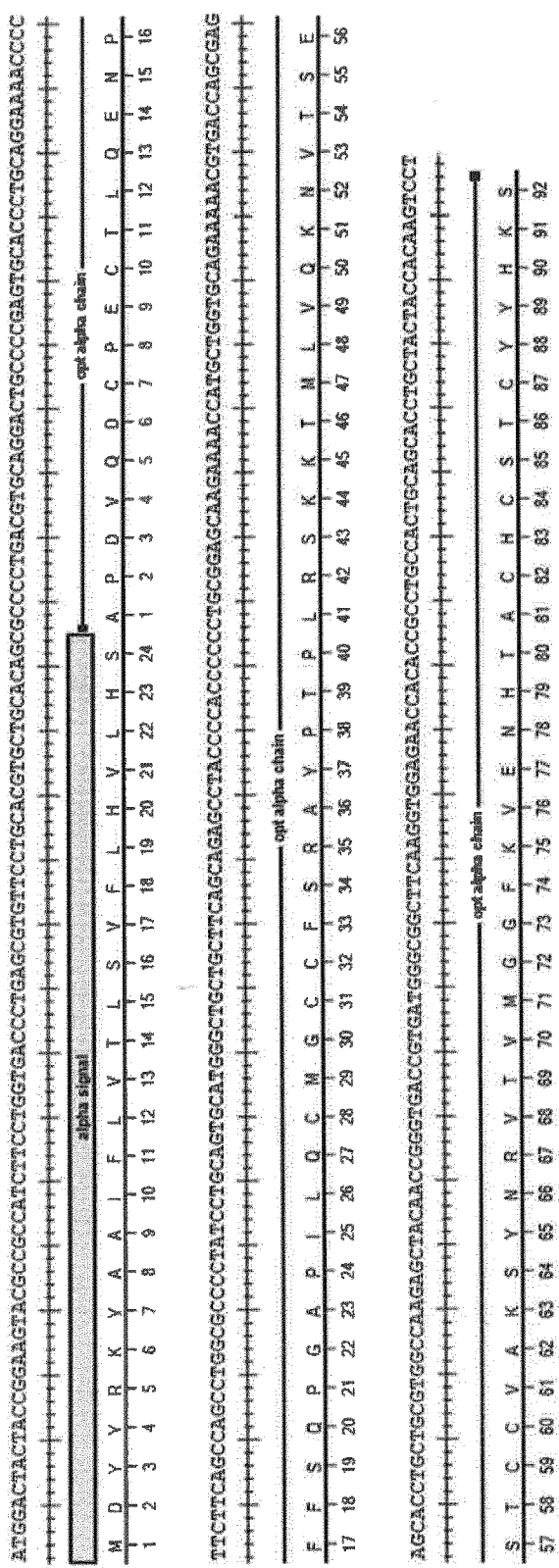

Fig 2 : Wild type Beta chain

Fig 3 : Nucleic Acid and Derived Amino Acid Sequences of ST3GAL4

Figs 4 and 5: Plasmid maps of the phCGalpha/beta and pST3 expression vectors. CMV = Cytomegalovirus promoter, BGHp(A) = Bovine Growth Hormone poly-adenylation sequence, f1 ori = f1 origin of replication, SV40 = Simian Virus 40 promoter, Neo = Neomycin resistance marker, Hyg = Hygromycin resistance marker, SV40 p(A) = Simian Virus 40 poly-adenylation sequence, hCG α = human chorionic gonadotropin alpha polypeptide, hCG β = human chorionic gonadotropin beta polypeptide, ST3GAL4 = α2,3-sialyltransferase, ST6GAL1 = α2,6-sialyltransferase, ColEI = ColEI origin of replication, Amp = ampicillin resistance marker.

Figure 4. phCG expression vector

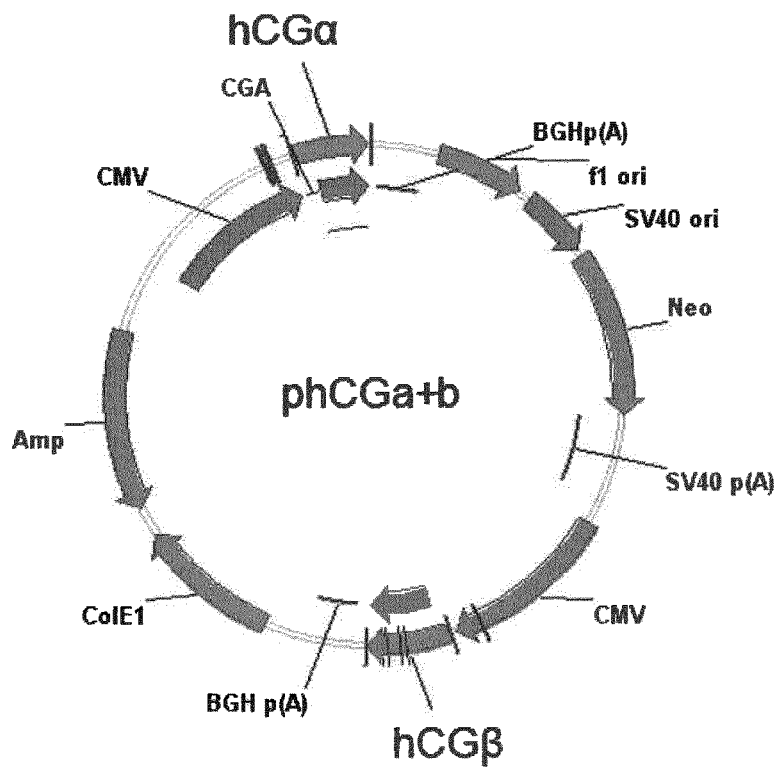

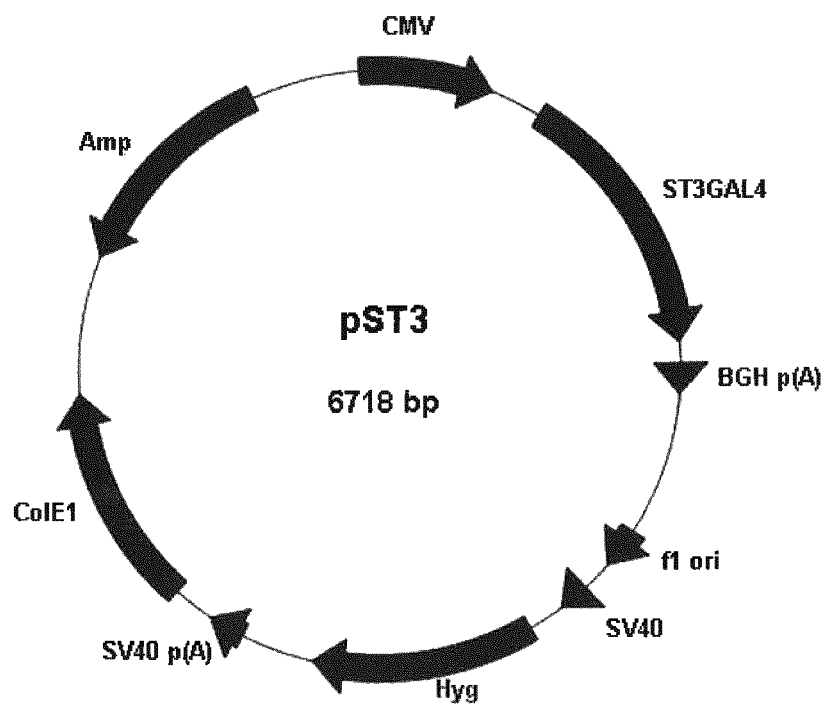
Figure 5. α2,3-sialyltransferase (ST3GAL4) expression vector

Figure 6: shows the detection of rhCG Isoforms by IEF stained with Coomassie Blue in compositions according to the invention (Lanes 4, 5, 6 and 7, 15 µg per lane); the CHO derived composition of the prior art, Ovitrelle (Lane 2, 15µg); and a human urinary product obtained from pregnant women Novarel (Lane 3, 15µg); IEF marker (Lane 1 (pI's from top: 7.0, 6.8, 6.5, 6.0, 5.1 and 4.75 respectively))

SEQUENCE LISTING

<160> NUMBER OF SEQ ID NOS: 14

<210> SEQ ID NO 1
<211> LENGTH: 349
<212> TYPE: DNA
<213> ORGANISM: Homo sapiens
<220> FEATURE:
<221> NAME/KEY: CDS
<222> LOCATION: (1)..(348)

<400> SEQUENCE: 1

| | | | | | | | | | | | | | | | | |
|---|---|---|---|---|---|---|---|---|---|---|---|---|---|---|---|---|
| atg | gac | tac | tac | cgg | aag | tac | gcc | gcc | atc | ttc | ctg | gtg | acc | ctg | agc | 48 |
| Met | Asp | Tyr | Tyr | Arg | Lys | Tyr | Ala | Ala | Ile | Phe | Leu | Val | Thr | Leu | Ser | |
| 1 | | | | 5 | | | | | 10 | | | | | 15 | | |
| gtg | ttc | ctg | cac | gtg | ctg | cac | agc | gcc | cct | gac | gtg | cag | gac | tgc | ccc | 96 |
| Val | Phe | Leu | His | Val | Leu | His | Ser | Ala | Pro | Asp | Val | Gln | Asp | Cys | Pro | |
| | | | 20 | | | | | 25 | | | | | 30 | | | |
| gag | tgc | acc | ctg | cag | gaa | aac | ccc | ttc | ttc | agc | cag | cct | ggc | gcc | cct | 144 |
| Glu | Cys | Thr | Leu | Gln | Glu | Asn | Pro | Phe | Phe | Ser | Gln | Pro | Gly | Ala | Pro | |
| | | 35 | | | | | 40 | | | | | 45 | | | | |
| atc | ctg | cag | tgc | atg | ggc | tgc | tgc | ttc | agc | aga | gcc | tac | ccc | acc | ccc | 192 |
| Ile | Leu | Gln | Cys | Met | Gly | Cys | Cys | Phe | Ser | Arg | Ala | Tyr | Pro | Thr | Pro | |
| | 50 | | | | | 55 | | | | | 60 | | | | | |
| ctg | cgg | agc | aag | aaa | acc | atg | ctg | gtg | cag | aaa | aac | gtg | acc | agc | gag | 240 |
| Leu | Arg | Ser | Lys | Lys | Thr | Met | Leu | Val | Gln | Lys | Asn | Val | Thr | Ser | Glu | |
| 65 | | | | | 70 | | | | | 75 | | | | | 80 | |
| agc | acc | tgc | tgc | gtg | gcc | aag | agc | tac | aac | cgg | gtg | acc | gtg | atg | ggc | 288 |
| Ser | Thr | Cys | Cys | Val | Ala | Lys | Ser | Tyr | Asn | Arg | Val | Thr | Val | Met | Gly | |
| | | | 85 | | | | | 90 | | | | | 95 | | | |
| ggc | ttc | aag | gtg | gag | aac | cac | acc | gcc | tgc | cac | tgc | agc | acc | tgc | tac | 336 |
| Gly | Phe | Lys | Val | Glu | Asn | His | Thr | Ala | Cys | His | Cys | Ser | Thr | Cys | Tyr | |
| | | 100 | | | | | 105 | | | | | 110 | | | | |
| tac | cac | aag | tcc | t | | | | | | | | | | | | 349 |
| Tyr | His | Lys | Ser | | | | | | | | | | | | | |
| | 115 | | | | | | | | | | | | | | | |

<210> SEQ ID NO 2
<211> LENGTH: 498
<212> TYPE: DNA
<213> ORGANISM: Homo sapiens

<400> SEQUENCE: 2

| | | | | | | |
|---|---|---|---|---|---|---|
| atggagatgt | tccaggggct | gctgctgttg | ctgctgctga | gcatgggcgg | gacatgggca | 60 |
| tccaaggagc | cgcttcggcc | acggtgccgc | cccatcaatg | ccaccctggc | tgtggagaag | 120 |
| gagggctgcc | ccgtgtgcat | caccgtcaac | accaccatct | gtgccggcta | ctgccccacc | 180 |
| atgacccgcg | tgctgcaggg | ggtcctgccg | gccctgcctc | aggtggtgtg | caactaccgc | 240 |
| gatgtgcgct | tcgagtccat | ccggctccct | ggctgcccgc | gcggcgtgaa | ccccgtggtc | 300 |
| tcctacgccg | tggctctcag | ctgtcaatgt | gcactctgcc | gccgcagcac | cactgactgc | 360 |
| gggggtccca | aggaccaccc | cttgacctgt | gatgaccccc | gcttccagga | ctcctcttcc | 420 |
| tcaaaggccc | ctcccccag | ccttccaagt | ccatcccgac | tcccggggcc | ctcggacacc | 480 |
| ccgatcctcc | cacaataa | | | | | 498 |

<210> SEQ ID NO 3
<211> LENGTH: 999
<212> TYPE: DNA
<213> ORGANISM: Homo sapiens

<400> SEQUENCE: 3

| | | | | | | |
|---|---|---|---|---|---|---|
| atgtgtcctg | caggctggaa | gctcctggcc | atgttggctc | tggtcctggt | cgtcatggtg | 60 |
| tggtattcca | tctcccggga | agacaggtac | atcgagcttt | ttatttttcc | catcccagag | 120 |
| aagaaggagc | cgtgcctcca | gggtgaggca | gagagcaagg | cctctaagct | ctttggcaac | 180 |
| tactcccggg | atcagcccat | cttcctgcgc | cttgaggatt | atttctgggt | caagacgcca | 240 |
| tctgcttacg | agctgcccta | tgggaccaag | gggagtgagg | atctgctcct | ccgggtgcta | 300 |

```
gccatcacca gctcctccat ccccaagaac atccagagcc tcaggtgccg ccgctgtgtg    360
gtcgtgggga acgggcaccg gctgcggaac agctcactgg gagatgccat caacaagtac    420
gatgtggtca tcagattgaa caatgcccca gtggctggct atgagggtga cgtgggctcc    480
aagaccacca tgcgtctctt ctaccctgaa tctgcccact tcgacccaa agtagaaaac    540 aacccagaca cactcctcgt cctggtagct ttcaaggcaa tggacttcca ctggattgag    600
accatcctga gtgataagaa gcgggtgcga aagggtttct ggaaacagcc tcccctcatc    660
tgggatgtca atcctaaaca gattcggatt ctcaaccccct tcttcatgga gattgcagct    720
gacaaactgc tgagcctgcc aatgcaacag ccacggaaga ttaagcagaa gcccaccacg    780
ggcctgttgg ccatcacgct ggccctccac ctctgtgact tggtgcacat tgccggcttt    840
ggctacccag acgcctacaa caagaagcag accattcact actatgagca gatcacgctc    900
aagtccatgg cggggtcagg ccataatgtc tcccaagagg ccctggccat taagcggatg    960
ctggagatgg gagctatcaa gaacctcacg tccttctga                          999

<210> SEQ ID NO 4
<211> LENGTH: 277
<212> TYPE: DNA
<213> ORGANISM: Homo sapiens

<400> SEQUENCE: 4
gcccctgacg tgcaggactg ccccgagtgc accctgcagg aaaacccctt cttcagccag     60
cctggcgccc ctatcctgca gtgcatgggc tgctgcttca gcagagccta ccccaccccc    120
ctgcggagca agaaaaccat gctggtgcag aaaaacgtga ccagcgagag cacctgctgc    180
gtggccaaga gctacaaccg ggtgaccgtg atgggcggct tcaaggtgga gaaccacacc    240
gcctgccact gcagcacctg ctactaccac aagtcct                             277

<210> SEQ ID NO 5
<211> LENGTH: 351
<212> TYPE: DNA
<213> ORGANISM: Homo sapiens

<400> SEQUENCE: 5
atggattact acagaaaata tgcagctatc tttctggtca cattgtcggt gtttctgcat     60
gttctccatt ccgctcctga tgtgcaggat tgcccagaat gcacgctaca ggaaaaccca    120
ttcttctccc agccgggtgc cccaatactt cagtgcatgg gctgctgctt ctctagagca    180
tatcccactc cactaaggtc caagaagacg atgttggtcc aaaagaacgt cacctcagag    240
tccacttgct gtgtagctaa atcatataac agggtcacag taatgggggg tttcaaagtg    300
gagaaccaca cggcgtgcca ctgcagtact tgttattatc acaaatctta a             351

<210> SEQ ID NO 6
<211> LENGTH: 116
<212> TYPE: PRT
<213> ORGANISM: Homo sapiens

<400> SEQUENCE: 6

Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45
```

```
Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
            115

<210> SEQ ID NO 7
<211> LENGTH: 165
<212> TYPE: PRT
<213> ORGANISM: Homo sapiens

<400> SEQUENCE: 7

Met Glu Met Phe Gln Gly Leu Leu Leu Leu Leu Leu Ser Met Gly
  1               5                  10                  15

Gly Thr Trp Ala Ser Lys Glu Pro Leu Arg Pro Arg Cys Arg Pro Ile
                 20                  25                  30

Asn Ala Thr Leu Ala Val Glu Lys Glu Gly Cys Pro Val Cys Ile Thr
                 35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 8
<211> LENGTH: 332
<212> TYPE: PRT
<213> ORGANISM: Homo sapiens

<400> SEQUENCE: 8

Met Cys Pro Ala Gly Trp Lys Leu Leu Ala Met Leu Ala Leu Val Leu
  1               5                  10                  15

Val Val Met Val Trp Tyr Ser Ile Ser Arg Glu Asp Arg Tyr Ile Glu
                 20                  25                  30

Leu Phe Tyr Phe Pro Ile Pro Glu Lys Lys Glu Pro Cys Leu Gln Gly
                 35                  40                  45

Glu Ala Glu Ser Lys Ala Ser Lys Leu Phe Gly Asn Tyr Ser Arg Asp
                 50                  55                  60

Gln Pro Ile Phe Leu Arg Leu Glu Asp Tyr Phe Trp Val Lys Thr Pro
 65                  70                  75                  80
```

Ser Ala Tyr Glu Leu Pro Tyr Gly Thr Lys Gly Ser Glu Asp Leu Leu
            85                  90                  95

Leu Arg Val Leu Ala Ile Thr Ser Ser Ile Pro Lys Asn Ile Gln
        100                 105                 110

Ser Leu Arg Cys Arg Cys Val Val Val Gly Asn Gly His Arg Leu
        115                 120                 125

Arg Asn Ser Ser Leu Gly Asp Ala Ile Asn Lys Tyr Asp Val Val Ile
130                 135                 140

Arg Leu Asn Asn Ala Pro Val Ala Gly Tyr Glu Gly Asp Val Gly Ser
145                 150                 155                 160

Lys Thr Thr Met Arg Leu Phe Tyr Pro Glu Ser Ala His Phe Asp Pro
                165                 170                 175

Lys Val Glu Asn Asn Pro Asp Thr Leu Leu Val Leu Val Ala Phe Lys
                180                 185                 190

Ala Met Asp Phe His Trp Ile Glu Thr Ile Leu Ser Asp Lys Lys Arg
            195                 200                 205

Val Arg Lys Gly Phe Trp Lys Gln Pro Leu Ile Trp Asp Val Asn
        210                 215                 220

Pro Lys Gln Ile Arg Ile Leu Asn Pro Phe Phe Met Glu Ile Ala Ala
225                 230                 235                 240

Asp Lys Leu Leu Ser Leu Pro Met Gln Gln Pro Arg Lys Ile Lys Gln
                245                 250                 255

Lys Pro Thr Thr Gly Leu Leu Ala Ile Thr Leu Ala Leu His Leu Cys
                260                 265                 270

Asp Leu Val His Ile Ala Gly Phe Gly Tyr Pro Asp Ala Tyr Asn Lys
            275                 280                 285

Lys Gln Thr Ile His Tyr Tyr Glu Gln Ile Thr Leu Lys Ser Met Ala
        290                 295                 300

Gly Ser Gly His Asn Val Ser Gln Glu Ala Leu Ala Ile Lys Arg Met
305                 310                 315                 320

Leu Glu Met Gly Ala Ile Lys Asn Leu Thr Ser Phe
                325                 330

<210> SEQ ID NO 9
<211> LENGTH: 92
<212> TYPE: PRT
<213> ORGANISM: Homo sapiens

<400> SEQUENCE: 9

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 10
<211> LENGTH: 116
<212> TYPE: PRT
<213> ORGANISM: Homo sapiens

<400> SEQUENCE: 10

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaggatccg ccaccatgtg tcctgcaggc tggaagc                              37

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttttttctt aagtcagaag gacgtgaggt tcttg                                35

<210> SEQ ID NO 13
<211> LENGTH: 500
<212> TYPE: DNA
<213> ORGANISM: Homo sapiens
<220> FEATURE:
<221> NAME/KEY: CDS
<222> LOCATION: (1)..(495)

<400> SEQUENCE: 13 atg gag atg ttc cag ggg ctg ctg ctg ttg ctg ctg agc atg ggc          48
Met Glu Met Phe Gln Gly Leu Leu Leu Leu Leu Leu Ser Met Gly
1               5                   10                  15 ggg aca tgg gca tcc aag gag ccg ctt cgg cca cgg tgc cgc ccc atc      96
Gly Thr Trp Ala Ser Lys Glu Pro Leu Arg Pro Arg Cys Arg Pro Ile
            20                  25                  30 aat gcc acc ctg gct gtg gag aag gag ggc tgc ccc gtg tgc atc acc      144
Asn Ala Thr Leu Ala Val Glu Lys Glu Gly Cys Pro Val Cys Ile Thr
        35                  40                  45 gtc aac acc acc atc tgt gcc ggc tac tgc ccc acc atg acc cgc gtg      192
Val Asn Thr Thr Ile Cys Ala Gly Tyr Cys Pro Thr Met Thr Arg Val
    50                  55                  60

```
ctg cag ggg gtc ctg ccg gcc ctg cct cag gtg gtg tgc aac tac cgc      240
Leu Gln Gly Val Leu Pro Ala Leu Pro Gln Val Val Cys Asn Tyr Arg
 65                  70                  75                  80 gat gtg cgc ttc gag tcc atc cgg ctc cct ggc tgc ccg cgc ggc gtg      288
Asp Val Arg Phe Glu Ser Ile Arg Leu Pro Gly Cys Pro Arg Gly Val
                     85                  90                  95 aac ccc gtg gtc tcc tac gcc gtg gct ctc agc tgt caa tgt gca ctc      336
Asn Pro Val Val Ser Tyr Ala Val Ala Leu Ser Cys Gln Cys Ala Leu
            100                 105                 110 tgc cgc cgc agc acc act gac tgc ggg ggt ccc aag gac cac ccc ttg      384
Cys Arg Arg Ser Thr Thr Asp Cys Gly Gly Pro Lys Asp His Pro Leu
        115                 120                 125 acc tgt gat gac ccc cgc ttc cag gac tcc tct tcc tca aag gcc cct      432
Thr Cys Asp Asp Pro Arg Phe Gln Asp Ser Ser Ser Ser Lys Ala Pro
    130                 135                 140 ccc ccc agc ctt cca agt cca tcc cga ctc ccg ggg ccc tcg gac acc      480
Pro Pro Ser Leu Pro Ser Pro Ser Arg Leu Pro Gly Pro Ser Asp Thr
145                 150                 155                 160 ccg atc ctc cca caa taagt                                            500
Pro Ile Leu Pro Gln
                165

<210> SEQ ID NO 14
<211> LENGTH: 1080
<212> TYPE: DNA
<213> ORGANISM: Homo sapiens
<220> FEATURE:
<221> NAME/KEY: CDS
<222> LOCATION: (52)..(1047)

<400> SEQUENCE: 14
gctagcgtta tctgcagaat tccaccacac tggactagtg gatccgccac c atg tgt    57
                                                         Met Cys
                                                           1 cct gca ggc tgg aag ctc ctg gcc atg ttg gct ctg gtc ctg gtc gtc    105
Pro Ala Gly Trp Lys Leu Leu Ala Met Leu Ala Leu Val Leu Val Val
            5                   10                  15 atg gtg tgg tat tcc atc tcc cgg gaa gac agg tac atc gag ctt ttt    153
Met Val Trp Tyr Ser Ile Ser Arg Glu Asp Arg Tyr Ile Glu Leu Phe
 20                  25                  30 tat ttt ccc atc cca gag aag aag gag ccg tgc ctc cag ggt gag gca    201
Tyr Phe Pro Ile Pro Glu Lys Lys Glu Pro Cys Leu Gln Gly Glu Ala
 35                  40                  45                  50 gag agc aag gcc tct aag ctc ttt ggc aac tac tcc cgg gat cag ccc    249
Glu Ser Lys Ala Ser Lys Leu Phe Gly Asn Tyr Ser Arg Asp Gln Pro
                 55                  60                  65 atc ttc ctg cgg ctt gag gat tat ttc tgg gtc aag acg cca tct gct    297
Ile Phe Leu Arg Leu Glu Asp Tyr Phe Trp Val Lys Thr Pro Ser Ala
             70                  75                  80 tac gag ctg ccc tat ggg acc aag ggg agt gag gat ctg ctc ctc cgg    345
Tyr Glu Leu Pro Tyr Gly Thr Lys Gly Ser Glu Asp Leu Leu Leu Arg
         85                  90                  95 gtg cta gcc atc acc agc tcc tcc atc ccc aag aac atc cag agc ctc    393
Val Leu Ala Ile Thr Ser Ser Ser Ile Pro Lys Asn Ile Gln Ser Leu
    100                 105                 110 agg tgc cgc cgc tgt gtg gtc gtg ggg aac ggg cac cgg ctg cgg aac    441
Arg Cys Arg Arg Cys Val Val Val Gly Asn Gly His Arg Leu Arg Asn
115                 120                 125                 130 agc tca ctg gga gat gcc atc aac aag tac gat gtg gtc atc aga ttg    489
Ser Ser Leu Gly Asp Ala Ile Asn Lys Tyr Asp Val Val Ile Arg Leu
                135                 140                 145
```

```
aac aat gcc cca gtg gct ggc tat gag ggt gac gtg ggc tcc aag acc      537
Asn Asn Ala Pro Val Ala Gly Tyr Glu Gly Asp Val Gly Ser Lys Thr
            150                 155                 160 acc atg cgt ctc ttc tac cct gaa tct gcc cac ttc gac ccc aaa gta      585
Thr Met Arg Leu Phe Tyr Pro Glu Ser Ala His Phe Asp Pro Lys Val
        165                 170                 175 gaa aac aac cca gac aca ctc ctc gtc ctg gta gct ttc aag gca atg      633
Glu Asn Asn Pro Asp Thr Leu Leu Val Leu Val Ala Phe Lys Ala Met
    180                 185                 190 gac ttc cac tgg att gag acc atc ctg agt gat aag aag cgg gtg cga      681
Asp Phe His Trp Ile Glu Thr Ile Leu Ser Asp Lys Lys Arg Val Arg
195                 200                 205                 210 aag ggt ttc tgg aaa cag cct ccc ctc atc tgg gat gtc aat cct aaa      729
Lys Gly Phe Trp Lys Gln Pro Pro Leu Ile Trp Asp Val Asn Pro Lys
                215                 220                 225 cag att cgg att ctc aac ccc ttc ttc atg gag att gca gct gac aaa      777
Gln Ile Arg Ile Leu Asn Pro Phe Phe Met Glu Ile Ala Ala Asp Lys
                230                 235                 240 ctg ctg agc ctg cca atg caa cag cca cgg aag att aag cag aag ccc      825
Leu Leu Ser Leu Pro Met Gln Gln Pro Arg Lys Ile Lys Gln Lys Pro
            245                 250                 255 acc acg ggc ctg ttg gcc atc acg ctg gcc ctc cac ctc tgt gac ttg      873
Thr Thr Gly Leu Leu Ala Ile Thr Leu Ala Leu His Leu Cys Asp Leu
    260                 265                 270 gtg cac att gcc ggc ttt ggc tac cca gac gcc tac aac aag aag cag      921
Val His Ile Ala Gly Phe Gly Tyr Pro Asp Ala Tyr Asn Lys Lys Gln
275                 280                 285                 290 acc att cac tac tat gag cag atc acg ctc aag tcc atg gcg ggg tca      969
Thr Ile His Tyr Tyr Glu Gln Ile Thr Leu Lys Ser Met Ala Gly Ser
                295                 300                 305 ggc cat aat gtc tcc caa gag gcc ctg gcc att aag cgg atg ctg gag     1017
Gly His Asn Val Ser Gln Glu Ala Leu Ala Ile Lys Arg Met Leu Glu
            310                 315                 320 atg gga gct atc aag aac ctc acg tcc ttc tgacttaagt ttaaaccgct       1067
Met Gly Ala Ile Lys Asn Leu Thr Ser Phe
            325                 330 gatcagcctc gac                                                      1080
```

OPTIMIZED NUCLEIC ACID SEQUENCES CODING FOR THE ALPHA-CHAIN OF HUMAN CHORIONIC GONADOTROPIN

SEQUENCE LISTING

The application contains a Sequence Listing which has been filed electronically in ASCII format and is hereby incorporated by reference in its entirety. Said ASCII copy, created on Feb. 19, 2019, is named 033236-0160_SL.txt and is 21,046 bytes in size.

CROSS-REFERENCE TO RELATED APPLICATIONS

This application is the U.S. National Stage of International Application PCT/EP2016/059006, filed Apr. 22, 2016, which claims priority from European Patent Application No. 15164965.4, filed Apr. 24, 2015.

The present invention relates to gonadotrophins for use in the treatment of infertility. In particular it relates to human chorionic gonadotrophin (hCG).

The gonadotrophins are a group of heterodimeric glycoprotein hormones which regulate gonadal function in the male and female. They include follicle stimulating hormone (FSH), luteinising hormone (LH) and chorionic gonadotrophin (CG).

Human chorionic gonadotrophin (hCG) is secreted mainly by human placenta during pregnancy and supports the maintenance of corpus luteum. hCG comprises a 92 amino acid alpha sub-unit (a chain), also common to the other glycoprotein hormones LH and FSH, and a 145 amino acid beta sub-unit (β chain) unique to hCG, which dictates the hormone specificity. Each sub-unit is post translationally modified by the addition of complex carbohydrate residues. The alpha sub-unit contains 2-N-linked glycosylation sites at amino acids 52 and 78 and the beta sub-unit contains 2-N-linked glycosylation sites at amino acids 13 and 30 and four O-linked glycosylation sites at amino acids 121, 127, 132 and 138.

hCG extracted from the urine of pregnant women [Choragon (Ferring)] has been used for many years in infertility treatment. The production of hCG extracted from urine involves the collection and processing of large amounts of urine. Ovitrelle (Serono), a recombinant version of hCG, is also available for use in infertility treatment. This recombinant product is expressed in Chinese hamster ovary (CHO) cells, and has a different pharmacokinetic profile to hCG produced from human urine.

There is considerable heterogeneity associated with hCG preparations which relates to differences in the amounts of various isoforms present. Individual hCG isoforms exhibit identical amino acid sequences but differ in the extent to which they are post-translationally modified; particular isoforms are characterised by heterogeneity of the carbohydrate branch structures and differing amounts of sialic acid (a terminal sugar) incorporation, both of which appear to influence the specific isoform bioactivity.

The glycosylation of recombinant hCG ("rhCG") products reflects the range of glycosyl-transferases present in the host cell line. The existing rhCG product, Ovitrelle, is derived from engineered Chinese hamster ovary cells (CHO cells). The range of glycan modifications in CHO derived rhCG are more limited than those found on the natural products, derived from urine. Examples of the reduced glycan heterogeneity found in CHO derived rhCG include a lack of bisecting glucosamine and a reduced content of core fucosylation and acetyl lactosamine extensions. In addition, CHO cells are only able to add sialic acid using the α2,3 linkage (Kagawa et al, 1988, Takeuchi et al, 1988, Svensson et al., 1990).

Human urinary hCG (that is, hCG extracted from the urine of pregnant women) which has been used to date in treatment of infertility is, in actual fact, placental hCG; hCG produced in the (human) placenta and then excreted in the urine. This hCG is extracted from urine for use as the pharmaceutical product. Bousfield et al (Rev Endocr Metab Disord (2011) 12:289-302) states that "while pituitary gonadotrophins possess both α2,3- and α2,6-linked sialic acid, placental hCG and recombinant gonadotrophins produced in Chinese hamster ovarian cells possess only α2,3-linked sialic acid". Thus, human urinary hCG (which is produced in the placenta) includes only α2,3-sialylation (like the CHO cell line derived recombinant products). Thus, the known pharmaceutical compositions which include hCG include only α2,3-linked sialic acid, but do not include α2,6-linked sialic acid.

It has been demonstrated that a recombinant FSH preparation (Organon) differs in the amounts of FSH with an isoelectric point (pI) of below 4 (considered the acidic isoforms) when compared to pituitary, serum or post-menopausal urine FSH (Ulloa-Aguirre et al. 1995). The amount of acidic isoforms in the urinary preparations of FSH was much higher as compared to the recombinant products, Gonal-f (Serono) and Puregon (Organon) (Andersen et al. 2004). This must reflect a lower molar content of sialic acid in rFSH since the content of negatively-charged glycan modified with sulphate is low in FSH. The lower sialic acid content, compared to natural FSH, is a feature of both commercially available FSH products and therefore must reflect a limitation in the manufacturing process (Bassett and Driebergen, 2005). The circulatory life-time of FSH has been documented for materials from a variety of sources. Some of these materials have been fractionated on the basis of overall molecular charge, as characterised by their pI, in which more acid equates to a higher negative charge. The major contributor to overall molecular charge is the total sialic content of each FSH molecule. For instance, rFSH (Organon) has a sialic acid content of around 8 mol/mol, whereas urine-derived FSH has a higher sialic acid content (de Leeuw et al. 1996). The corresponding plasma clearance rates in the rat are 0.34 and 0.14 ml/min (Ulloa-Aguirre et al. 2003). In another example where a sample of recombinant FSH was split into high and low pI fractions, the in vivo potency of the high pI (lower sialic acid content) fraction was decreased and it had a shorter plasma half-life (D'Antonio et al. 1999). The applicants have found that, similar to FSH, the known, CHO derived, recombinant hCG product (e.g. Ovitrelle) also has a lower amount of hCG with an isoelectric point (pI) of below 4 (considered the acidic isoforms) than urinary hCG, also reflecting a lower sialic acid content of the known rhCG product compared to urinary hCG.

The applicants have developed a human derived recombinant hCG (that is, a recombinant hCG which is produced or expressed in a human cell line, e.g. made by engineering a human cell line) which has a more acidic profile than the CHO cell line derived rhCG product, Ovitrelle, and which has a higher sialic acid content. This rhCG is the subject of International patent Application No. PCT/GB2010/001854, published as WO 2011/042688. Recombinant hCG with a mixture of both α2,3 and α2,6-linked sialic acid was made by engineering a human cell line to express both rhCG and α2,3 sialyltransferase. The expressed product is highly acidic, having a sialic acid content [expressed in terms of a ratio of moles of sialic acid to moles of protein] of for example 19.1 mol/mol, and carries a mix of both α2,3- and α2,6-linked sialic acids; the latter provided by the endogenous sialyl transferase activity. The applicants' research indicates that the type of sialic acid linkage, α2,3- or α2,6-, can have a dramatic influence on biological clearance of hCG. Human cell lines, as opposed to CHO cell lines, can express recombinant hCG with sialic acids attached by both α2,3 and α2,6 linkages.

The cell line of WO 2011/042688 expresses human derived recombinant hCG well. However, the cell line also expresses a relatively high level of the free β chain (free beta sub unit), and purification (to remove this free β chain from product hCG) was required.

The applicants have now developed a new cell line which expresses both rhCG and α2,3 sialyltransferase, and which produces rhCG with a reduced amount of the free β chain, thereby improving yield and reducing the level of product purification required (see FIG. 7).

According to the present invention there is provided a (e.g. host) cell characterized in that it comprises integrated into its genome a (nucleic acid) sequence coding for the α chain of hCG selected from: a sequence according to SEQ ID NO: 1; a sequence which has at least 96.5% homology with the sequence of SEQ ID NO:1 (e.g. a sequence which has at least 96.5% sequence identity with the sequence of SEQ ID NO:1); a sequence which has at least 97% homology with (e.g. at least 98% or at least 99% homology with) the sequence of SEQ ID NO:1 (e.g. a sequence which has at least 97% sequence identity with (e.g. at least 98% or at least 99% sequence identity with) the sequence of SEQ ID NO:1); a sequence according to SEQ ID NO. 4; a sequence which has at least 96.5% homology with the sequence of SEQ ID NO: 4 (e.g. a sequence which has at least 96.5% sequence identity with the sequence of SEQ ID NO:4); and a sequence which has at least 97% homology with (e.g. at least 98% or at least 99% homology with) the sequence of SEQ ID NO:4 (e.g. a sequence which has at least 97% sequence identity with (e.g. at least 98% or at least 99% sequence identity with) the sequence of SEQ ID NO:4). Preferably the (nucleic acid) sequence coding for the α chain of hCG is not the sequence which is banked as AH007338 (that is, preferably, the (nucleic acid) sequence coding for the α chain of hCG is not that shown in SEQ ID NO:5). The cell may further comprise integrated into its genome a cDNA encoding an alpha-2,3-sialyltransferase, for example a sequence according to SEQ ID NO: 3. The cell may further comprise integrated into its genome a (nucleic acid) sequence coding for the β chain of hCG, for example the sequence according to SEQ ID NO:2.

The host cell may be, for example, a PER.C6® cell, a HT1080 cell, a GT-5s cell etc. Preferably the cell is a PER.C6® cell such as a PER.C6® cell deposited under ECACC no. 96022940.

According to the present invention there is provided a PER.C6® cell such as a PER.C6® cell deposited under ECACC no. 96022940, characterized in that it further comprises integrated into its genome a (nucleic acid) sequence coding for the α chain of hCG. The (nucleic acid) sequence coding for the α chain of hCG may be selected from: a sequence according to SEQ ID NO: 1; a sequence which has at least 90% homology with the sequence of SEQ ID NO:1 (e.g. a sequence which has at least 90% sequence identity with the sequence of SEQ ID NO:1); a sequence which has at least 97% homology with (e.g. at least 98% or at least 99% homology with) the sequence of SEQ ID NO:1 (e.g. a sequence which has at least 97% sequence identity with (e.g. at least 98% or at least 99% sequence identity with) the sequence of SEQ ID NO:1); a sequence according to SEQ ID NO. 4; a sequence which has at least 90% homology with the sequence of SEQ ID NO: 4 (e.g. a sequence which has at least 90% sequence identity with the sequence of SEQ ID NO:4); and a sequence which has at least 97% homology with (e.g. at least 98% or at least 99% homology with) the sequence of SEQ ID NO:4 (e.g. a sequence which has at least 97% sequence identity with (e.g. at least 98% or at least 99% sequence identity with) the sequence of SEQ ID NO:4). Preferably the (nucleic acid) sequence coding for the α chain of hCG is not the sequence which is banked as AH007338. The cell may further comprise integrated into its genome a cDNA encoding an alpha-2,3-sialyltransferase, for example a sequence according to SEQ ID NO: 3. The cell may further comprise integrated into its genome a (nucleic acid) sequence coding for the β chain of hCG, for example the sequence according to SEQ ID NO:2.

It will be appreciated that the term "a sequence coding for the α chain of hCG" or "a (nucleic acid) sequence coding for the α chain of hCG" used herein also refers to a sequence coding for the α chain of FSH (or a sequence coding for the α chain of LH) because the α chain of hCG is the same as that for FSH (and LH).

The term "nucleic acid sequence" herein relates to any nucleic acid molecule that codes for polypeptides such as peptides, proteins etc. These nucleic acid molecules may be made of DNA, RNA or analogues thereof. However, nucleic acid molecules being made of DNA are preferred.

The person skilled in the art is clearly aware that modification of a starting nucleotide sequence describes the process of optimization with respect to codon usage. The changes introduced can be easily identified by comparing the modified sequence and the starting sequence. Moreover, both sequences (that is, the starting sequence and the optimised sequence) will code for the same amino acid sequence.

The amino acid sequence of the α-chain of human hCG is disclosed in WO2011/042688 (referred to as SEQ ID1 in that document), and is that described in Fiddes and Goodman 1979. It is banked under AH007388, and is shown as SEQ ID NO. 5 below. The amino acid sequence of the β-chain of human hCG is depicted in SEQ ID No.2, and is banked as NP_000728. These amino acid sequences correspond to the wild-type amino acid sequences of the α- and the β-chain of human hCG. The terms "wild-type nucleic acid sequence" or "starting nucleic acid sequence" for the purposes of the present invention relate to a nucleic acid sequence which is intended to be used for (over)expression in a host cell and which has not been adapted to the codon usage in the host cell, but is the actual wild-type nucleic acid sequence coding for the protein. The term "optimized nucleic acid sequence" for the purposes of the present invention relates to a sequence that has been modified for expression in a host cell by adapting the sequence of the nonmodified/starting nucleic acid sequence. An optimized nucleic acid sequence codes for a protein having the same amino acid sequence as the protein encoded by the non-modified sequence. The applicants have developed a optimised sequences which code for the α-chain of hCG (see e.g. SEQ ID No. 1 and 4, FIG. 1).

According to the present invention in a further aspect there is provided a polynucleotide sequence (e.g. a polynucleotide sequence coding for the α chain of hCG) comprising a sequence selected from a nucleic acid sequence according to SEQ ID NO: 1; a nucleic acid sequence according to SEQ ID NO: 4; a nucleic acid sequence with at least 97% homology with (e.g. at least 98% or at least 99% homology with) the nucleic acid of SEQ ID NO: 1 (e.g. a nucleic acid sequence with at least 97% sequence identity with (e.g. at least 98% or at least 99% sequence identity with) the nucleic acid of SEQ ID NO: 1); and a nucleic acid sequence with at least 97% homology with (e.g. at least 98% or at least 99% homology with) the nucleic acid of SEQ ID NO: 4 (e.g. a nucleic acid sequence with at least 97% sequence identity with (e.g. at least 98% or at least 99% sequence identity with) the nucleic acid of SEQ ID NO: 4).

According to the present invention in a further aspect there is provided a method for producing recombinant hCG in a cell, comprising culturing the cell in a suitable medium and harvesting the recombinant protein (hCG) from said cell and/or said medium (e.g. harvesting the recombinant hCG from the cell culture supernatant), wherein the cell (host cell) comprises integrated into its genome a (nucleic acid) sequence coding for the α chain of hCG selected from: a sequence according to SEQ ID NO: 1; a sequence which has at least 90% homology with the sequence of SEQ ID NO:1 (e.g. a sequence which has at least 90% sequence identity with the sequence of SEQ ID NO:1); a sequence which has at least 97% homology with (e.g. at least 98% or at least 99% homology with) the sequence of SEQ ID NO:1 (e.g. a sequence which has at least 97% sequence identity with (e.g. at least 98% or at least 99% sequence identity with) the sequence of SEQ ID NO:1); a sequence according to SEQ ID NO. 4; a sequence which has at least 90% homology with the sequence of SEQ ID NO: 4 (e.g. a sequence which has at least 90% sequence identity with the sequence of SEQ ID NO:4); and a sequence which has at least 97% homology with (e.g. at least 98% or at least 99% homology with) the sequence of SEQ ID NO:4 (e.g. a sequence which has at least 97% sequence identity with (e.g. at least 98% or at least 99% sequence identity with) the sequence of SEQ ID NO:4). Preferably the (nucleic acid) sequence coding for the α chain of hCG is not the sequence which is banked as AH007338. The cell may further comprise integrated into its genome a cDNA encoding an alpha-2,3-sialyltransferase, for example a sequence according to SEQ ID NO: 3. The cell may further comprise integrated into its genome a (nucleic acid) sequence coding for the β chain of hCG, for example the sequence according to SEQ ID NO:2. The method may include a further step or steps of purifying the recombinant hCG obtained from said cell and/or said medium (e.g. purifying the recombinant hCG from the cell culture supernatant).

The (host) cell may be, for example, a PER.C6® cell, a HT1080 cell, a GT-5s cell etc. Preferably the cell is a PER.C6® cell such as a PER.C6® cell deposited under ECACC no. 96022940.

According to the present invention in a further aspect there is provided a method for producing recombinant hCG in a cell, comprising culturing the cell in a suitable medium and harvesting the recombinant protein (hCG) from said cell and/or said medium (e.g. harvesting the recombinant hCG from the cell culture supernatant), wherein the cell is a PER.C6® cell (such as a PER.C6® cell deposited under ECACC no. 96022940) comprising integrated into its genome a (nucleic acid) sequence coding for the α chain of hCG. The (nucleic acid) sequence coding for the α chain of hCG may be selected from: a sequence according to SEQ ID NO: 1; a sequence which has at least 90% homology with the sequence of SEQ ID NO:1 (e.g. a sequence which has at least 90% sequence identity with the sequence of SEQ ID NO:1); a sequence which has at least 97% homology with (e.g. at least 98% or at least 99% homology with) the sequence of SEQ ID NO:1 (e.g. a sequence which has at least 97% sequence identity with (e.g. at least 98% or at least 99% sequence identity with) the sequence of SEQ ID NO:1); a sequence according to SEQ ID NO. 4; a sequence which has at least 90% homology with the sequence of SEQ ID NO: 4 (e.g. a sequence which has at least 90% sequence identity with the sequence of SEQ ID NO:4); and a sequence which has at least 97% homology with (e.g. at least 98% or at least 99% homology with) the sequence of SEQ ID NO:4 (e.g. a sequence which has at least 97% sequence identity with (e.g. at least 98% or at least 99% sequence identity with) the sequence of SEQ ID NO:4). Preferably the (nucleic acid) sequence coding for the α chain of hCG is not the sequence which is banked as AH007338. The cell may further comprise integrated into its genome a cDNA encoding an alpha-2,3-sialyltransferase, for example a sequence according to SEQ ID NO: 3. The cell may further comprise integrated into its genome a (nucleic acid) sequence coding for the β chain of hCG, for example the sequence according to SEQ ID NO:2. The method may include a further step or steps of purifying the recombinant hCG obtained from said cell and/or said medium (e.g. purifying the recombinant hCG from the cell culture supernatant).

The term "host cell" for the purposes of the present invention refers to any cell that is commonly used for expression, i.e. transcription and translation of nucleic acid sequences for the production of e.g. polypeptides. In particular, the term "host cell" or "organism" relates to prokaryotes, lower eukaryotes, plants, insect cells or mammalian cell culture systems. Preferably, the host cell is a mammalian cell, more preferably the host cell is a human cell, even more preferably a PERC6® cell.

The term "recombinant nucleic acid molecule" within the meaning of the present invention is intended to comprise all kinds of nucleic acid molecules which are capable of being introduced into a host cell and effecting the expression of a nucleic acid sequence which is contained within the recombinant nucleic acid molecule. The term includes, for example, plasmid vectors and viral vectors (e.g. adenoviral, lentiviral and retroviral vectors), as are well known in the art.

According to the present invention in a further aspect there is provided a recombinant nucleic acid molecule comprising a (first) nucleic acid sequence coding for the α chain of hCG, which (first) nucleic acid sequence is selected from a sequence according to SEQ ID NO: 1; a sequence which has at least 96.5% homology with the sequence of SEQ ID NO:1 (e.g. a sequence which has at least 96.5% sequence identity with the sequence of SEQ ID NO:1); a sequence which has at least 97% homology with (e.g. at least 98% or at least 99% homology with) the sequence of SEQ ID NO:1 (e.g. a sequence which has at least 97% sequence identity with (e.g. at least 98% or at least 99% sequence identity with) the sequence of SEQ ID NO:1); a sequence according to SEQ ID NO. 4; a sequence which has at least 96.5% homology with the sequence of SEQ ID NO: 4 (e.g. a sequence which has at least 96.5% sequence identity with the sequence of SEQ ID NO:14; and a sequence which has at least 97% homology with (e.g. at least 98% or at least 99% homology with) the sequence of SEQ ID NO:4 (e.g. a sequence which has at least 97% sequence identity with (e.g. at least 98% or at least 99% sequence identity with) the sequence of SEQ ID NO:4). Preferably, the recombinant nucleic acid molecule of this aspect of the present invention comprises both an optimised nucleic acid sequence coding for the α-chain of human hCG and a nucleic acid sequence coding for the β-chain of hCG. Preferably, the (first) nucleic acid sequence is under the control of a promoter which is active in a host cell. Preferably the recombinant nucleic acid molecule further comprises a second nucleic acid sequence coding for the β chain of hCG. The second nucleic acid sequence coding for the β chain of hCG may be the sequence according to SEQ ID No. 2.

The second nucleic acid sequence may be under the control of a separate promoter which is active in a host cell. The first nucleic acid sequence and/or the second nucleic acid sequence may be under the control of a viral promoter (e.g. a CMVie promoter).

According to the present invention in a further aspect there is provided a host cell comprising or including a recombinant nucleic acid molecule as set out above (e.g. a host cell comprising a recombinant nucleic acid molecule comprising a (first) nucleic acid sequence coding for the α chain of hCG, which (first) nucleic acid sequence is selected from a sequence according to SEQ ID NO: 1; a sequence which has at least 96.5% homology with the sequence of SEQ ID NO:1 (e.g. a sequence which has at least 96.5% sequence identity with the sequence of SEQ ID NO:1); a sequence which has at least 97% homology with (e.g. at least 98% or at least 99% homology with) the sequence of SEQ ID NO:1 (e.g. a sequence which has at least 97% sequence identity with (e.g. at least 98% or at least 99% sequence identity with) the sequence of SEQ ID NO:1); a sequence according to SEQ ID NO. 4; a sequence which has at least 96.5% homology with the sequence of SEQ ID NO: 4 (e.g. a sequence which has at least 96.5% sequence identity with the sequence of SEQ ID NO:4); and a sequence which has at least 97% homology with (e.g. at least 98% or at least 99% homology with) the sequence of SEQ ID NO:4 (e.g. a sequence which has at least 97% sequence identity with (e.g. at least 98% or at least 99% sequence identity with) the sequence of SEQ ID NO:4).

The applicants have found that the cells (host cells), cell lines incorporating these host cells, recombinant nucleic acid molecules, polynucleotides and methods of the invention may produce recombinant hCG in high yield and purity (e.g. with little free beta chain).

According to the present invention in a further aspect there is provided a recombinant hCG ("rhCG" or "rechCG") which includes α2,3- and α2,6-sialylation, wherein the recombinant hCG is produced in a cell as described and claimed herein. The recombinant hCG may have a sialic acid content [expressed in terms of a ratio of moles of sialic acid to moles of protein] of from 12 mol/mol to 20 mol/mol, for example from 12 mol/mol to 15.5 mol/mol, for example 12 mol/mol to 14.9 mol/mol. The rhCG (or rhCG preparation) may have a sialic acid content of 12.5 mol/mol to 14.5 mol/mol, for example a sialic acid content of 12.8 mol/mol to 13.2 mol/mol. The rhCG (or rhCG preparation) according to the invention may have a sialic acid content of 13 mol/mol.

In examples of the invention, the rhCG may be present as a single isoform or as a mixture of isoforms.

The recombinant hCG (or rhCG preparation) produced by the methods and cells of the invention includes α2,3- and α2,6-sialylation. By sialylation it is meant the amount of sialic residues present on the hCG carbohydrate structures. α2,3-sialylation means sialylation at the 2,3 position (as is well known in the art); and α2,6 sialylation means sialylation at the 2,6 position (also well known in the art). Thus, herein, the wording "% of the total sialylation may be a 2,3 sialylation" refers to the % of the total number of sialic acid residues present in the hCG which are sialylated in the 2,3 position. The term "% of the total sialylation being α2,6-sialylation" refers to the % of the total number of sialic acid residues present in the hCG which are sialylated in the 2,6 position. The term "% of the total sialylation being α2,8-sialylation" refers to the % of the total number of sialic acid residues present in the hCG which are sialylated in the 2,8 position.

The rhCG (or rhCG preparation) produced by the methods and cells according to the invention may have 1% to 99% of the total sialylation being α2,3-sialylation. The rhCG (or rhCG preparation) produced by the methods and cells according to the invention may have 1% to 90% of the total sialylation being α2,3-sialylation. The rhCG (or rhCG preparation) according to the invention may have 10% or more of the total sialylation being α2,3-sialylation, for example, 10% to 90% of the total sialylation may be α2,3-sialylation. For example, 20, 30, 40, 45, 50, 55, 60, 70, 80 or 90% or more of the total sialylation may be α2,3-sialylation. 45% to 80% of the total sialylation may be α2,3-sialylation, for example 50% to 70% of the total sialylation may be α2,3-sialylation, for example 55 to 65% of the total sialylation may be α2,3-sialylation. The rhCG (or rhCG preparation) may include α2,3-sialylation in an amount which is from 65 to 95% of the total sialylation, for example from 70 to 90% of the total sialylation, for example from 85 to 90% of the total sialylation.

The rhCG (or rhCG preparation) produced by the methods and cells of the invention may have 1 to 99% of the total sialylation being α2,6-sialylation. The rhCG (or rhCG preparation) of the invention may have 5 to 50% of the total sialylation being α2,6-sialylation. For example 5 to 45%, for example 6 to 40%, for example 7 to 30%, for example 8 to 20% of the total sialylation may be α2,6-sialylation. The rhCG (or rhCG preparation) may include α2,6-sialylation in an amount which is from 20-75% of the total sialylation, for example, 30-60% of the total sialylation, for example 35-45% of the total sialylation. The rhCG (or rhCG preparation) may include α2,6-sialylation in an amount which is from 5 to 35% of the total sialylation, for example from 10 to 20% of the total sialylation. For example 11-55% of the total sialylation may be α2,6-sialylation.

The rhCG or rhCG preparation produced by the methods and cells may optionally further include α2,8 sialylation. The rhCG (or rhCG preparation) of the invention may have 5% or less of the total sialylation being α2,8-sialylation, for example 0 to 4%, e.g. 0.1-4% of the total sialylation may be α2,8-sialylation. The rhCG (or rhCG preparation) of the invention may have no α2,8-sialylation.

The rhCG (or rhCG preparation) produced by the methods and cells according to the invention may have a sialic acid content (amount of sialylation per hCG molecule) of (based on the mass of protein, rather than the mass of protein plus carbohydrate) of 6% or greater (e.g. between 6% and 15%, e.g. between 7% and 13%, e.g. between 8% and 12%, e.g. between 11% and 15%, e.g. between 12% and 14%) by mass.

The rhCG (or rhCG preparation) may be produced or expressed in a human cell line, for example a PER.C6® cell line, a HT1080 cell line etc. The rhCG (or rhCG preparation) may be produced or expressed in a human derived cell line or a modified human cell line, for example a PER.C6® derived cell line or modified PER.C6® cell line, a modified HT1080 cell line or HT1080 derived cell line etc. In a preferred example, the rhCG is produced or expressed in a PER.C6® cell line, a PER.C6® derived cell line or a modified PER.C6® cell line. rhCG which is produced or expressed in a human cell line (e.g. a PER.C6® cell line, a HT1080 cell line, a GT-5s cell line) will include some α2,6-linked sialic acids (α2,6 sialylation) provided by endogenous sialyl transferase activity [of the cell line] and will include some α2,3-linked sialic acids (α2,3 sialylation) provided by endogenous sialyl transferase activity [of the cell line]. The cell line may be modified using α2,3-sialyltransferase. Alternatively or additionally, the cell line may be modified using α2,6-sialyltransferase. This may simplify (and render more efficient) the production method because manipulation and control of e.g. the cell growth medium to retain sialylation may be less critical than with known processes. The method may also be more efficient because there is little basic rhCG produced compared to production of known rhCG products; more acidic rhCG is produced and separation/removal of basic hCG is less problematic.

The rhCG may be produced using an α2,3-sialyltransferase, for example produced using a human cell line modified using an α2,3-sialyltransferase. The rhCG may include α2,6-linked sialic acids (α2,6 sialylation) provided by endogenous sialyl transferase activity. The rhCG may be produced using an α2,3- and/or an α2,6-sialyltransferase, for example produced using a human cell line modified using an α2,3-sialyltransferase and/or an α2,6-sialyltransferase.

According to the present invention in a further aspect there is provided a recombinant hCG or a recombinant hCG preparation as described herein which is produced or expressed by the methods described herein.

The rhCG structure contains glycan moieties. Branching can occur with the result that the glycan may have 1, 2, 3, 4 or more terminal sugar residues or "antennae", as is well known in the art. The rhCG according to aspects of the invention of the invention may have glycans with mono-antennary and/or di-antennary and/or tri-antennary and/or tetra-antennary glycan structures. The rhCG may include mono-antennary and/or bi-antennary and/or tri-antennary and/or tetra-antennary glycan structures, for example with relative amounts as follows: 0.1 to 3% mono-antennary; 65% to 85% bi-antennary; 15 to 25% tri-antennary and 0.5 to 1.5% tetra-antennary (e.g. as shown by WAX analysis of charged glycans).

According to the present invention in a further aspect there is provided a pharmaceutical composition comprising a recombinant hCG (rhCG) having α2,3-sialylation and α2,6-sialylation, wherein the recombinant hCG is produced by the methods and/or cells disclosed herein. The rhCG may have a sialic acid content [expressed in terms of a ratio of moles of sialic acid to moles of protein] of from 12 mol/mol to 15.5 mol/mol, for example 12 mol/mol to 14.9 mol/mol (e.g. as set out above). The rhCG may have a sialic acid content of 12.5 mol/mol to 14.5 mol/mol, for example a sialic acid content of 12.8 mol/mol to 13.2 mol/mol. Preferably the rhCG according to the invention has a sialic acid content of 13 mol/mol.

The pharmaceutical composition may further comprise FSH and/or LH.

FSH can be obtained by any means known in the art. FSH as used herein includes human-derived and recombinant FSH. Human-derived FSH can be purified from any appropriate source (e.g. urine) by any method known in the art. The FSH may be recombinant FSH—for example expressed in a human cell line. Methods of expressing and purifying recombinant FSH are well known in the art.

LH can be obtained by any means known in the art. LH, as used herein, includes human-derived and recombinant LH. Human-derived LH can be purified from any appropriate source (e.g. urine) by any method known in the art. Methods of expressing and purifying recombinant LH are known in the art.

The pharmaceutical composition may be for, or for use in, the treatment of infertility, e.g. for use in e.g. assisted reproductive technologies (ART), ovulation induction or intrauterine insemination (IUI). The pharmaceutical composition may be for, or for use in, triggering final maturation/ovulation and luteinization, the stimulation of follicular development in women with severe LH and FSH deficiency, and/or in luteal support (rhCG/rLH). The pharmaceutical composition may be for, or for use in, inducing monofollicular development in anovulatory WHO Type II women (e.g. rhCG with rLH), for enhancing multifollicular response with LH priming in patients undergoing COH (e.g. rhCG with rLH), and for supplementation to COH to improve implantation/pregnancy rates (e.g. rhCG with rLH), and/or increasing pregnancy rates in assisted reproductive technologies. The pharmaceutical composition may be for, or for use in, the prevention of miscarriages, and/or prematurity prevention. The pharmaceutical composition may be for, or for use in, the treatment of endometriosis.

The pharmaceutical composition may be used, for example, in medical indications where known hCG preparations are used. The present invention also provides the use of rhCG and/or an rhCG preparation described herein (according to aspects of the invention) for, or in the manufacture of a medicament for, the treatment of infertility.

The pharmaceutical compositions of the present invention may be formulated into well-known compositions for any route of drug administration, e.g. oral, rectal, parenteral, transdermal (e.g. patch technology), intravenous, intramuscular, subcutaneous, intracisternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others. Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. The compositions of the present invention also can contain additives such as but not limited to preservatives, wetting agents, emulsifying agents, and dispersing agents. Antibacterial and antifungal agents can be included to prevent growth of microbes and includes, for example, m-cresol, benzyl alcohol, paraben, chlorobutanol, phenol, sorbic acid, and the like. Furthermore, it may be desirable to include isotonic agents such as sugars, sodium chloride, and the like.

In some cases, to effect prolonged action it is desirable to slow the absorption of hCG (and other active ingredients, if present) from subcutaneous or intramuscular injection. This can be accomplished by the use of a liquid suspension of crystalline or amorphous material with poor water solubility. The rate of absorption of hCG then depends upon its rate of dissolution which, in turn, can depend upon crystal size and crystalline form. Alternatively, delayed absorption of a parenterally administered hCG combination form is accomplished by dissolving or suspending the hCG combination in an oil vehicle. Injectable depot forms can be made by forming microencapsule matrices of the hCG (and other agents, if present) in biodegradable polymers such as polylactide-polyglycolide. Depending upon the ratio of hCG to polymer and the nature of the particular polymer employed, the rate of hCG release can be controlled. Examples of other biodegradable polymers include polyvinylpyrrolidone, poly (orthoesters), poly(anhydrides) etc. Depot injectable formulations are also prepared by entrapping the hCG in liposomes or microemulsions which are compatible with body tissues. Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

Formulations (e.g. injectable formulation can be supplied as a product having pharmaceutical compositions containing hCG (optionally with FSH, LH etc.) If there is more than one active ingredient (i.e. hCG and e.g. FSH or LH) these may be suitable for administration separately or together. If administered separately, administration can be sequential. The product can be supplied in any appropriate package. For example, a product can contain a number of pre-filled syringes or vials containing either hCG, FSH, or a combination of both FSH and hCG. The syringes or vials may be packaged in a blister package or other means to maintain sterility. A product can optionally contain instructions for using the hCG and FSH formulations.

The pH and exact concentration of the various components of the pharmaceutical composition are adjusted in accordance with routine practice in this field. See GOODMAN and GILMAN's THE PHARMACOLOGICAL BASIS FOR THERAPEUTICS, 7$^{th}$ ed. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an embodiment, the parenteral compositions are supplied in dosage unit form for ease of administration and uniformity of dosage.

DETAILED DESCRIPTION OF THE INVENTION

The present invention will now be described in more detail with reference to the following Examples and to the attached drawings in which:

FIG. 1 shows the nucleic acid (SEQ ID NO: 1) and derived amino acid (SEQ ID NO: 6) sequences of the optimised hCG alpha sequence;

FIG. 2 shows the nucleic acid (SEQ ID NO: 13) and derived amino acid sequences of hCG beta sequence (SEQ ID NO: 7);

FIG. 3 shows the nucleic acid (SEQ ID NO: 14) and derived amino acid sequences of ST3GAL4 (SEQ ID NO: 8)

FIG. 4 shows a plasmid map of the phCGalpha/beta expression vector;

FIG. 5 shows the α2,3-sialyltransferase (ST3GAL4) expression vector;

Figure 6:
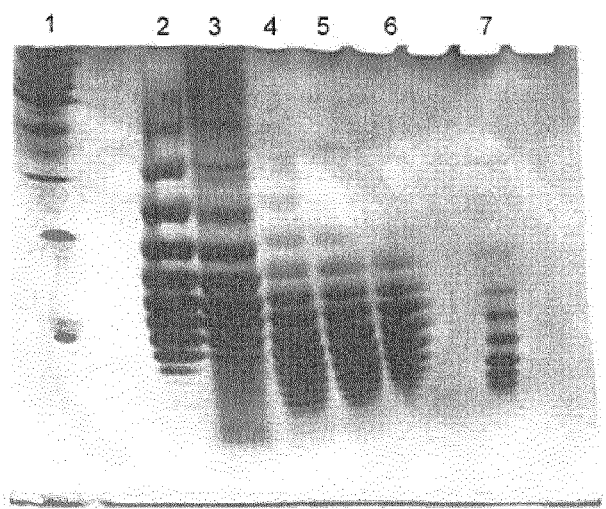
Figure 7:
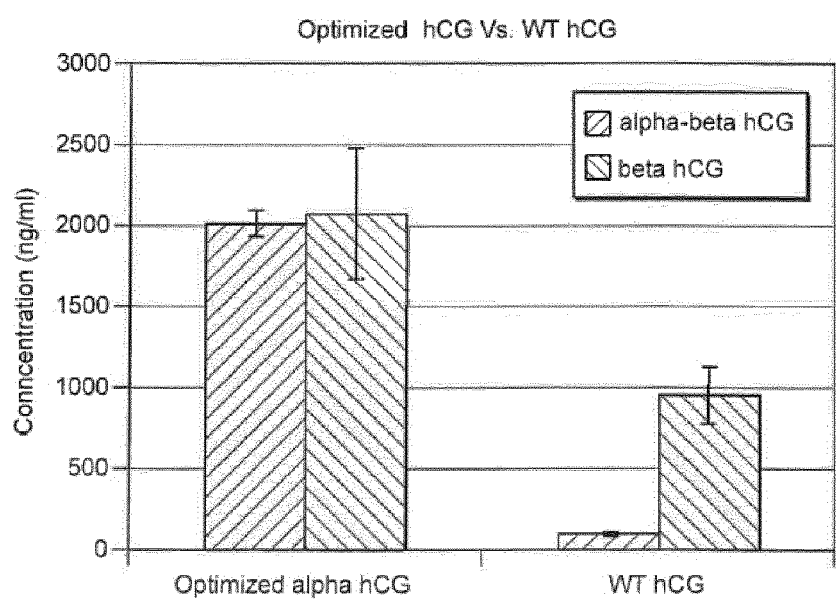

FIG. 6 shows the detection of rhCG Isoforms by IEF stained with Coomassie Blue in compositions according to the invention (Lanes 4, 5, 6 and 7, 15 µg per lane); the CHO derived composition of the prior art, Ovitrelle (Lane 2, 15 µg); and a human urinary product obtained from pregnant women Novarel (Lane 3, 15 µg); and FIG. 7 compares the concentration of hCG ("alpha-beta hCG") and free beta chain ("beta hCG") produced using the cells of the invention including the "Optimised" nucleic sequence of the alpha sub unit, compared with concentration of hCG ("alpha-beta hCG") and free beta chain ("beta hCG") produced in comparative example cells including the WT (wild-type) alpha sub unit;

EXAMPLES 1 TO 7

Overview of Cell Line Development Process

A single plasmid carrying hCG alpha and beta chains, each driven from a separate CMVie promoter, was transfected into PER.C6® cells by electroporation.

This plasmid carried a neomycin resistance gene cassette (FIG. 4) allowing for selection of transfectants using G418 (Geneticin). Pools of transfectants were expanded and then subjected to limiting dilution cloning in 96 well plates under G418 selection. Clonal lines were expanded and high expressing colonies were identified based on hCG titre in the cell culture supernatant.

Five lead clones were selected, based on high productivity, and each was then transfected with a second plasmid expressing the α2,3-sialyltransferase gene ST3GAL4 along with the Hygromycin selection maker (FIG. 5). Each of the five transfection pools was expanded and cell culture supernatants were assessed for hCG concentration and in vivo pharmacokinetics (PK).

Promising pools were then subjected to another round of limited dilution cloning. The resulting clones were expanded and cell culture supernatants were assessed for hCG concentration and exposed galactose on the hCG protein (by lectin ELISA). Those with a low level of exposed galactose were subjected to further assays including in vivo PK. Clones that produced hCG with optimum PK profiles, had low exposed galactose and expressed the protein at high levels were assessed and selected for productivity and growth characteristics.

Example 1

Sequence Selection and Plasmid Vectors

The coding region of the gene for the hCG alpha polypeptide is shown in FIG. 1. The coding region of the gene for the hCG alpha polypeptide sequence is referred to herein SEQ ID NO: 1.

The coding region of the gene for hCG beta polypeptide was used according to Fiddes and Goodman (1980). The sequence is banked as NP_000728 and is consistent with the protein sequences of CGbeta3, CGbeta5 and CGbeta7. The sequence is referred to herein as SEQ ID NO: 2

The coding region of the gene for beta-galactoside alpha-2,3-sialyltransferase 4 (α2,3-sialyltransferase, ST3GAL4) was used according to Kitagawa and Paulson (1994). The sequence is banked as L23767 and referred to herein as SEQ ID NO: 3.

Two plasmids were used: the first, phCG, co-expresses hCG alpha and beta chains; and the second, expresses the sialyltransferase gene ST3GAL4.

Example 2a

Construction of the hCG Expression Vector phCG is a synthetic alpha chain of hCG, optimised for codon usage in mammalian cells including the native hCG alpha signal peptide. It may be engineered by methods well known in the art.

Figure 2:
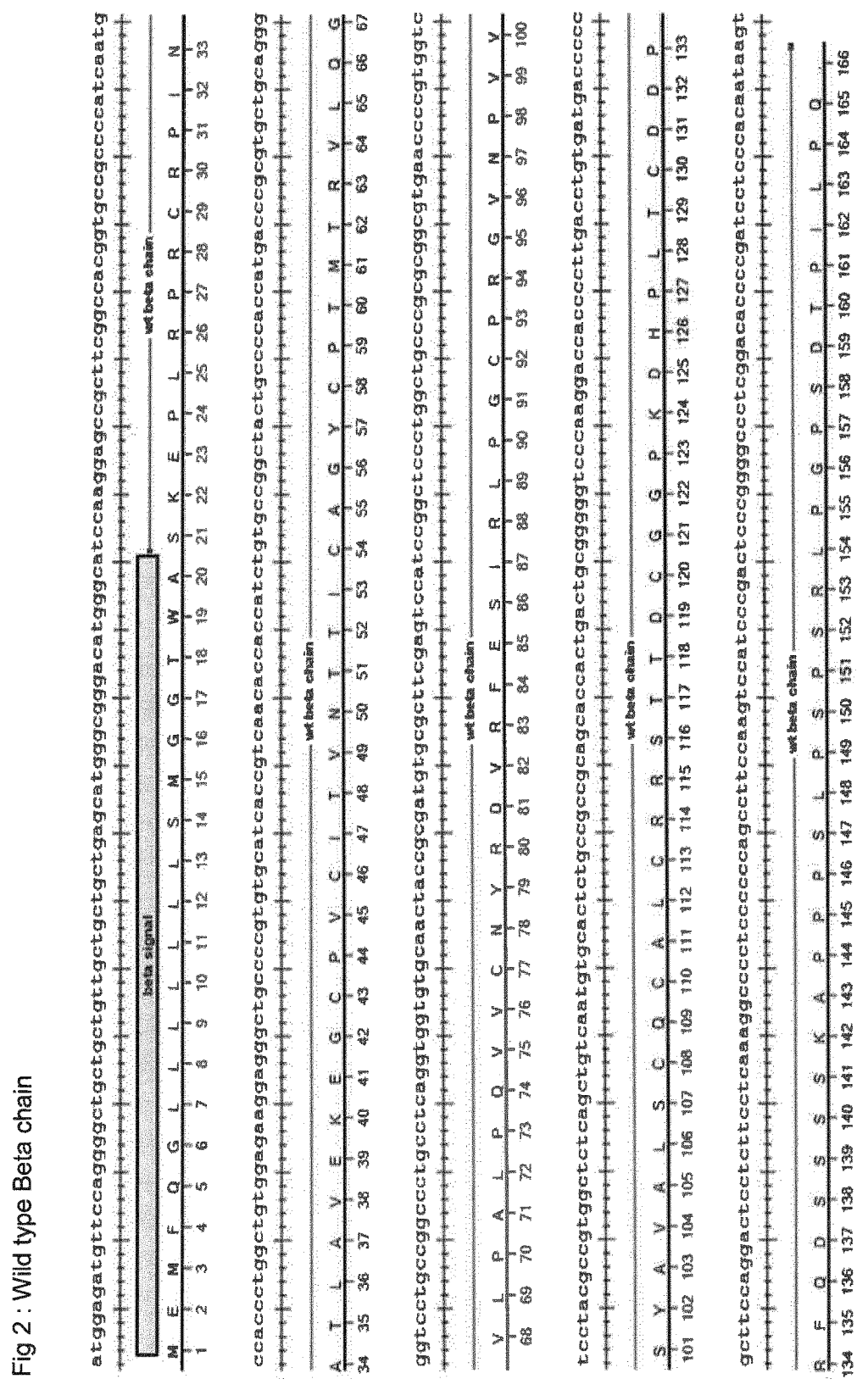

The coding sequence of hCG alpha polypeptide (SEQ ID NO: 1) and hCG beta polypeptide (NP_000728, SEQ ID NO: 2) were amplified by PCR using methods well known in the art (see, for example, International Patent Application published as WO2011/042688). The phCG alpha DNA was digested with BamHI and NheI and inserted into the sites BamHI and NheI on a CMV driven mammalian expression vector (Crucell vector pcDNA3002Neo). This placed the gene in the correct orientation for expression driven by a CMVie promoter with a downstream BGH polyA signal. The native hCG beta gene including native signal peptide was digested with the restriction enzymes AscI and HpaI and inserted into the AscI and HpaI sites so that expression would be driven by a second CMVie promoter with an additional downstream BGH poly A signal. The vector backbone also included a neomycin resistance maker as well as elements required for selection and replication in prokaryotic cells. The vector was amplified and sequenced using general methods are known in the art. Sequences of the optimised hCG alpha and native (wild-type) beta chains are given in FIGS. 1 and 2, respectively.

All colonies selected for sequencing contained the correct sequences according to SEQ ID NO: 1 and SEQ ID NO: 2. Plasmid phCG A+B was selected for transfection (FIG. 4).

Example 2b

Construction of the ST3 Expression Vector

The ST3GAL4 gene is expressed in pST3. The coding sequence of beta-galactoside alpha-2,3-sialyltransferase 4 (ST3, L23767, SEQ ID NO: 3, FIG. 3) was amplified by PCR using the primer combination 2,3STfw and 2,3STrev.

```
2,3STfw
                                       (SEQ ID NO: 11)
5'-CCAGGATCCGCCACCATGTGTCCTGCAGGCTGGAAGC-3'

2,3STrev
                                       (SEQ ID NO: 12)
5'-TTTTTTTCTTAAGTCAGAAGGACGTGAGGTTCTTG-3'
```

The resulting amplified ST3 DNA was digested with the restriction enzymes BamHI and AflII and inserted into the BamHI and AflII sites on the CMV driven mammalian expression vector carrying a hygromycin resistance marker (vector pcDNA3002Neo) so that it is located downstream of CMVie promoter and upstream of BGH polyA sequence. The vector backbone also included a hygromycin resistance maker as well as elements required for selection and replication in prokaryotic cells. The vector was amplified as previously described and sequenced. Clone pST3#1 (FIG. 5) contained the correct sequence according to SEQ ID NO: 3 and was selected for transfection.

Example 3

Plasmid Transfection

The plasmid phCG (FIG. 4), which has a single PvuI site located in the prokaryotic beta-lactamase gene, was linearised with PvuI (New England Biolabs Cat. No. R0150). Linearized plasmid DNA was transfected into PER.C6® cells as follows.

Cell cultures were maintained in complete PERMAB medium (CD4PERMAB (Hyclone Cat. No. SH30871.01) supplemented with L-glutamine to 3 mM final concentration (Invitrogen Cat. No. 25030-123) and Pluronic F68 at 1.0 g/L final concentration (Invitrogen Cat. No. 24040-032) in 250 ml Erlenmeyer flasks. Cells were maintained in a shaking incubator (Kuhner Climo-shaker ISF1-X) set at 100 rpm, 5% $CO_2$ and 37° C., for at least 14 days prior to transfection. 48 hours prior to transfection, cells were transferred into fresh medium at a density of $0.5 \times 10^6$ cells/ml.

On the day of transfection, cells were counted in a Beckman Coulter ViCell XR to determine cell density and to ensure viability was >90%. Cells were harvested by centrifugation and resuspended in fresh PERMAB medium before being mixed with linearized phCG DNA. The cell/DNA mix was electro-shocked in the chamber of an electroporator set at 250V for 5 msec, before being quickly transferred to 10 ml of pre-warmed PERMAB medium. This process was repeated a total of 6 times and all 6 transfections were pooled into a single T-175 $cm^2$ tissue culture flask. The flask was placed in a static incubator set at 37° C., 5% $CO_2$. After 48 hours, cells were resuspended in the appropriate volume of selective PERMAB (complete PERMAB medium+G418 (125 µg/ml)) to give a viable cell density of $0.5 \times 10^6$/ml.

The pool culture was passaged twice weekly, maintaining cells at a density of $0.3 \times 10^6$ cell/ml in selective medium until cell viability had increased to >50%. At this point, cells were transferred to shaking cultures in 250 ml Erlenmeyer flasks. After several weeks in shaking culture, pool supernatant was sampled and assayed for hCG concentration. Once it was established that the pool was positive for hCG expression, cells were prepared for limited dilution cloning.

A cell suspension at 0.3 viable cells/ml was prepared in PERMAB medium supplemented with G-418 at 125 µg/ml. The cell suspension was dispensed into 96 well flat bottomed tissue culture plates at 200 µl/well and incubated in a humidified atmosphere at 37° C., 5% $CO_2$ (Binder CB150). Plates were scanned regularly using the Genetix Clone Select Imager to track the growth of cells in each well.

After two weeks, 535 wells were identified that contained actively growing colonies of cells. Supernatants from these wells were sampled and assayed for hCG using a commercial kit (DRG diagnostics HCG ELISA Cat. No. EIA1469). Based on the results from these assays, a total of 162 of the colonies were transferred into 24 well plates containing 0.5 ml/well selective PERMAB medium. When cells in the wells were near to confluency, supernatant from each of the 162 wells was sampled and assayed for hCG levels. Based on these results, 91 of the best expressing cell lines were selected for expansion into T-25 flasks. These cell lines were again grown to near confluence, at which point supernatants were sampled and assayed for hCG as above. Based on these results, the 58 best expressing cell lines were expanded into T-75 flasks. Specific production rate (SPR) analysis was performed on each of these 58 cell lines by methods known in the art and specific productivity was expressed in pg/cell/day.

Thus, in this Example a plasmid incorporating hCG alpha and beta chains was transfected into PER.C6 ® cells and transfectants were selected using medium containing G418. Growing colonies of cells were screened for hCG concentration in the supernatant and those expressing the highest level were expanded further. After subsequent rounds of expansion and screening, 20 clones that expressed hCG were selected for growth and productivity studies. Based on the results of these studies, 5 clones were selected for transfection with a second plasmid incorporating the ST3GAL4 gene.

Example 4

Transfection with the ST3GAL4 Plasmid pST3

Stable clones were generated as previously described in Example 3.

Figure 3:
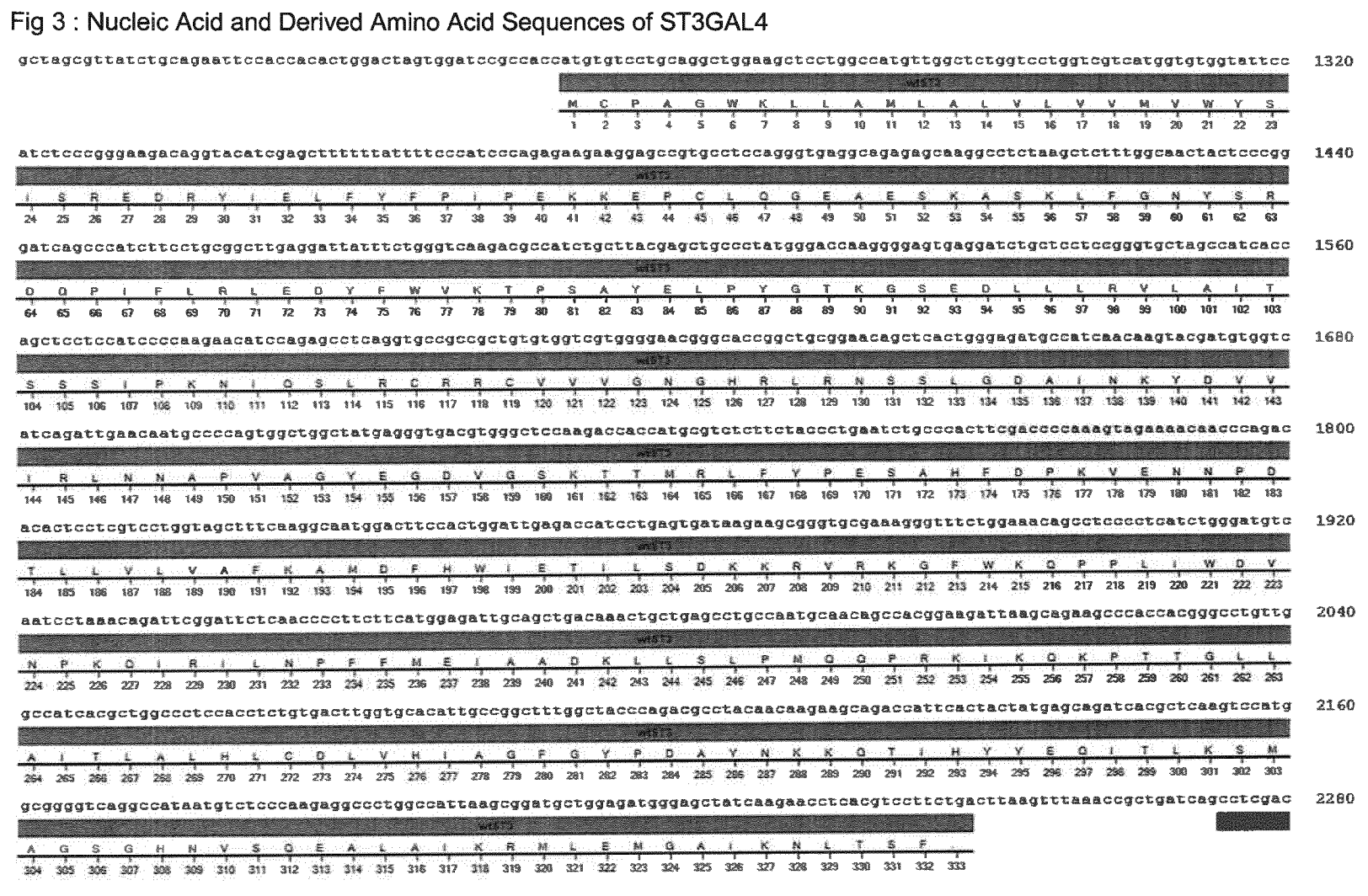

The five best clones produced by the method as described in Example 3 were selected for transfection with the ST3GAL4 plasmid pST3 (see Example 2, FIGS. 3 and 5). Transfection was performed by electroporation using the same method described in Example 3, except that transformants were selected in complete PERMAB medium supplemented with Hygromycin at 0.5 µg/ml instead of G418. Using this method, five pools were obtained that expressed hCG.

Samples of supernatants from the transfection pools were assessed in a rat pharmacokinetic model and, based on this data along with data from the RCA-lectin binding assay (measuring exposed galactose on the hCG chains), a single pool was selected for further limited dilution cloning, by methods known in the art.

This dilution cloning yielded >600 clones each of which was also screened for hCG expression and the degree of exposed galactose as measured by RCA-lectin binding. Those clones with the lowest levels of exposed galactose were expanded further and samples were subjected to in vivo PK and corroborating lectin binding data. Five clones derived from the single pool were further assessed for growth and productivity characteristics.

Each of these clones was expanded and a seed stock cell bank was made following standard cryopreservation procedures. Stocks from the seed stock cell bank were thawed and found to be viable.

Example 5

Analysis by Isoelectric Focussing

Electrophoresis is defined as the transport of charged molecules through a solvent by an electrical field. The mobility of a biological molecule through an electric field will depend on the field strength, net charge on the molecule, size and shape of the molecule, ionic strength and properties of the medium through which the molecules migrate.

Isoelectric focusing (IEF) is an electrophoretic technique for the separation of proteins based on their pI. The pI is the pH at which a protein has no net charge and will not migrate in an electric field. The sialic acid content of the hCG isoforms subtly alters the pI point for each isoform, which can be exploited using this technique to visualise the Per.C6 hCG isoforms from each clone.

The isoelectric points of the Per.C6 produced hCG isoforms were analyzed using isoelectric focussing. Per.C6 hCG was produced as described in Example 6.

Per.C6 hCG samples were separated on Novex® IEF Gels containing 5% polyacrylamide under native conditions on a pH 3.0-7.0 gradient in an ampholyte solution pH 3.0-7.0. Proteins were visualised using Coomassie Blue staining, using methods well known in the art.

FIG. 6 shows the detection of rhCG Isoforms by IEF stained with Coomassie Blue in compositions produced according to the invention produced from the cloned cell lines made by the method set out in Examples 6 (Lanes 4, 5, 6 and 7, 15 µg per lane); the CHO derived composition of the prior art, Ovitrelle (Lane 2, 15 µg); and a human urinary product obtained from pregnant women Novarel (Lane 3, 15 µg). The bands represent isoforms of hCG containing different numbers of sialic acid molecules. FIG. 6 indicates that human cell line derived recombinant hCG engineered with α2,3-sialyltransferase (compositions according to the invention) is more acidic than Ovitrelle and urinary hCG from pregnant women.

FIG. 7 compares the concentration of hCG ("alpha-beta hCG") and free beta chain ("beta hCG") produced using the cells of the invention (that is, using cell lines made by the method set out in Examples 1 to 4) which include the "Optimised" alpha sub unit, compared with concentration of hCG ("alpha-beta hCG") and free beta chain ("beta hCG") produced in comparative example cells including the WT (wild-type) alpha sub unit. FIG. 7 shows that the cells of the invention express high amounts of hCG and low excess of the free beta subunit. In other words, the yield and purity of recombinant hCG produced by the cells and methods of the invention is markedly improved.

Table A indicates the percentage of free β-hCG Subunits in semi-purified samples of various batches of hCG produced using the cells of the invention (that is, using cell lines made by the method set out in Examples 1 to 4) which include the "Optimised" alpha sub unit ("Opt. alpha hCG"), compared with the percentage of free β-hCG Subunits in semi-purified samples of hCG produced in comparative example cells including the WT (wild-type) alpha sub unit ("WT alpha hCG"), as determined by Hydrophobic Phenyl-5PW HPLC chromatography.

Table A shows that the cells of the invention express high amounts of hCG and a rather lower excess of the free beta subunit (5.7-10.6%) compared to cells including the WT alpha sub unit (64-66%). In other words, the yield and purity of recombinant hCG produced by the cells and methods of the invention is markedly improved.

TABLE A

| Clone | % Free ß-hCG (PHE-5PW) |
|---|---|
| WT alpha hCG (1G2) | 64.1 |
| WT alpha hCG (1G2) | 66.0 |
| Opt. alpha hCG (13.8) | 5.7 |
| Opt. alpha hCG (29) | 7.5 |
| Opt. alpha hCG (29) | 6.6 |
| Opt. alpha hCG (29) | 10.6 |

Example 6

Production and Purification Overview

A procedure was developed to produce recombinant hCG in PER.C6 cells that were cultured in suspension in serum free medium. The procedure is described below and was applied to several hCG-producing PER.C6 cell lines.

Recombinant hCG from an α2,3-sialyltransferase transfected clone was prepared using the methods of Examples 1 to 4 described above.

The cells were grown in shaker flasks in 6GRO medium (SAFC) until a cell density of $1\times10^6$ to $3\times10^6$ cells/ml was achieved. The cells were transferred to a 5 L glass stirred tank bioreactor with a density of about 1×10⁶ cells/ml. The bioreactor worked in perfusion mode using a Proper1 media (Lonza).

Thereafter, purification of the product rhCG was carried out using various ultrafiltration steps, anion and cation exchange capture chromatography, hydrophobic chromatography and pseudo-affinity chromatography, by methods well known in the art.

During all chromatographic procedures, the presence of immunoreactive recombinant hCG was confirmed by ELISA (DRG EIA 1469) and IEF (Example 5).

Example 7

Sialic Acid Content

Sialic acid is a protein-bound carbohydrate considered to be a mono-saccharide and occurs in combination with other mono-saccharides like galactose, mannose, glucosamine, galactosamine and fucose. The total sialic acid on purified rhCG according to the invention was measured using a method based on the method of Stanton et. al. (J. Biochem. Biophys. Methods. 30 (1995), 37-48).

The total sialic acid content of samples of Per.C6 recombinant hCG modified with α2,3-sialyltransferase (produced by the methods of Example 4 and 6) were measured and the results are in Table 1 below [expressed in terms of a ratio of moles of sialic acid to moles of protein].

Example 8 hCG Bioassay According to USP

A hCG Bioassay was carried out, in order to determine the hCG specific activity, for each of the samples of Table 1 below. The activity was measured according to USP (USP Monographs: Chorionic Gonadotropin, USPC Official Aug. 1, 2009 -Nov. 30, 2009), using Ovitrelle as a standard. Ovitrelle has a biological activity of 26,000 IU/mg (Curr Med Res Opin. 2005 December; 21(12): 1969-76). The acceptance limit was >21,000 IU hCG/mg. The biological activity for samples of human cell line derived hCG recombinant hCGs engineered with α2,3-sialyltransferase are shown in Table 1.

TABLE 1

| Sample | 1 | 2 | 3 | 4 | 5 | 6 |
|---|---|---|---|---|---|---|
| Sialic acid (SA) content (μmol SA/μmolhCG) | 13 | 13 | 13 | 13 | 13 | 15 |
| Potency IU/mg | 25363 | 25009 | 24904 | 24623 | 25645 | 26623 |
| % Potency (Ovitrelle 26000 IU/mg) | 97.5 | 96.2 | 95.8 | 94.7 | 98.6 | 102.4 |

| Sample | 7 | 8 | 9 | 10 | 11 |
|---|---|---|---|---|---|
| Sialic acid (SA) content (μmol SA/μmolhCG) | 14 | 14 | 13 | 13 | 13 |
| Potency IU/mg | 27227 | 26142 | 26539 | 26181 | 24230 |
| % Potency (Ovitrelle 26000 IU/mg) | 104.7 | 100.5 | 102 | 101 | 93.2 |

As seen above, the potency is similar to, and may be greater than, Ovitrelle (see e.g. Sample 7).

REFERENCES

Andersen C Y, Westergaard L G, and van Wely M. (2004). FSH isoform composition of commercial gonadotrophin preparations: a neglected aspect? Reprod Biomed Online. 9(2), 231-236.

Bassett R M, and Driebergen R. (2005). Continued improvements in the quality and consistency of follitropin alfa, recombinant human FSH. Reprod Biomed Online. 10(2), 169-177.

D'Antonio M., Borrelli F., Datola A., Bucci R., Mascia M., Polletta P., Piscitelli D., and Papoian R. (1999) Biological characterization of recombinant human follicle stimulating hormone isoforms. Human Reproduction 14, 1160-1167

Fiddes, J. C. and Goodman, H. M. (1979) Isolation, cloning and sequence analysis of the cDNA for the alpha-subunit of human chorionic gonadotropin. Nature, 281, 351-356.

Fiddes, J. C. and Goodman, H. M. (1980) The cDNA for the beta-subunit of human chorionic gonadotropin suggests evolution of a gene by readthrough into the 3'-untranslated region. Nature, 286, 684-387.

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol Chem. 263(33), 17508-17515.

Lowry O H, Rosebrough N J, Farr A L, Randall R J. (1951) Protein measurement with the Folin phenol reagent. J Biol Chem. 193(1), 265-75.

Lowry, P J, McLean, C, Jones R L and Satgunasingam N. (1976) Purification of anterior pituitary and hypothalamic hormones Clin Pathol Suppl (Assoc Clin Pathol). 7, 16-21.

Royle L, Radcliffe C M, Dwek R A and Rudd P M (2006) Methods in Molecular Biology, ed I Brockhausen-Schutzbach (Humana Press), 347: Glycobiology protocols, 125-144.

Steelman S L, and Pohley F M. (1953) Assay of the follicle stimulating hormone based on the augmentation with human chorionic gonadotropin. Endocrinology. 53(6), 604-616.

Svensson E C, Soreghan B, and Paulson J C. (1990) Organization of the beta-galactoside alpha 2,6-sialyltransferase gene. Evidence for the transcriptional regulation of terminal glycosylation. J Biol Chem. 265(34):20863-20868.

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol Chem. 263(8), 3657-3663.

Ulloa-Aguirre A, Midgley A R Jr, Beitins I Z, and Padmanabhan V. (1995). Follicle-stimulating isohormones: characterization and physiological relevance. Endocr Rev. 16(6), 765-787.

Ulloa-Aguirre A, Timossi C, Barrios-de-Tomasi J, Maldonado A, and Nayudu P. (2003). Impact of carbohydrate heterogeneity in function of follicle-stimulating hormone: studies derived from in vitro and in vivo models. Biol Reprod. 69(2), 379-389.

Optimised hCG alpha
Nucleotide sequence of optimised hCG alpha
(SEQ ID NO: 1)
```
  1 ATGGACTACT ACCGGAAGTA CGCCGCCATC TTCCTGGTGA CCCTGAGCGT GTTCCTGCAC

61 GTGCTGCACA GCGCCCCTGA CGTGCAGGAC TGCCCCGAGT GCACCCTGCA GGAAAACCCC

121 TTCTTCAGCC AGCCTGGCGC CCCTATCCTG CAGTGCATGG GCTGCTGCTT CAGCAGAGCC

181 TACCCCACCC CCCTGCGGAG CAAGAAAACC ATGCTGGTGC AGAAAAACGT GACCAGCGAG

241 AGCACCTGCT GCGTGGCCAA GAGCTACAAC CGGGTGACCG TGATGGGCGG CTTCAAGGTG

301 GAGAACCACA CCGCCTGCCA CTGCAGCACC TGCTACTACC ACAAGTCCT
```
Protein sequence of hCG optimised alpha (SEQ ID NO: 6)
```
  1 MDYYRKYAAI FLVTLSVFLH VLHSAPDVQD CPECTLQENP FFSQPGAPIL QCMGCCFSRA 61 YPTPLRSKKT MLVQKNVTSE STCCVAKSYN RVTVMGGFKV ENHTACHCST CYYHKS
```
Human Chorionic Gonadotrophin beta polypeptide Accession number NP_000728

Nucleotide sequence of hCG beta
(SEQ ID NO: 2)
Nucleotide sequence
```
  1 ATGGAGATGT TCCAGGGGCT GCTGCTGTTG CTGCTGCTGA GCATGGGCGG GACATGGGCA

61 TCCAAGGAGC CGCTTCGGCC ACGGTGCCGC CCCATCAATG CCACCCTGGC TGTGGAGAAG

121 GAGGGCTGCC CCGTGTGCAT CACCGTCAAC ACCACCATCT GTGCCGGCTA CTGCCCCACC

181 ATGACCCGCG TGCTGCAGGG GGTCCTGCCG GCCCTGCCTC AGGTGGTGTG CAACTACCGC

241 GATGTGCGCT TCGAGTCCAT CCGGCTCCCT GGCTGCCCGC GCGGCGTGAA CCCCGTGGTC

301 TCCTACGCCG TGGCTCTCAG CTGTCAATGT GCACTCTGCC GCCGCAGCAC CACTGACTGC

361 GGGGGTCCCA AGGACCACCC CTTGACCTGT GATGACCCCC GCTTCCAGGA CTCCTCTTCC

421 TCAAAGGCCC CTCCCCCCAG CCTTCCAAGT CCATCCCGAC TCCCGGGGCC CTCGGACACC

481 CCGATCCTCC CACAATAA
```
Protein sequence of hCG beta (SEQ ID NO: 7)
```
  1 MEMFQGLLLL LLLSMGGTWA SKEPLRPRCR PINATLAVEK EGCPVCITVN TTICAGYCPT

61 MTRVLQGVLP ALPQVVCNYR DVRFESIRLP GCPRGVNPVV SYAVALSCQC ALCRRSTTDC

121 GGPKDHPLTC DDPRFQDSSS SKAPPPSLPS PSRLPGPSDT PILPQ
```
Beta-galactoside alpha-2,3-sialyltransferase 4

Accession Number L23767

Nucleotide sequence of ST3GAL4
(SEQ ID NO: 3)
```
  1 ATGTGTCCTG CAGGCTGGAA GCTCCTGGCC ATGTTGGCTC TGGTCCTGGT CGTCATGGTG

61 TGGTATTCCA TCTCCCGGGA AGACAGGTAC ATCGAGCTTT TTTATTTTCC CATCCCAGAG

121 AAGAAGGAGC CGTGCCTCCA GGGTGAGGCA GAGAGCAAGG CCTCTAAGCT CTTTGGCAAC

181 TACTCCCGGG ATCAGCCCAT CTTCCTGCGG CTTGAGGATT ATTTCTGGGT CAAGACGCCA

241 TCTGCTTACG AGCTGCCCTA TGGGACCAAG GGGAGTGAGG ATCTGCTCCT CCGGGTGCTA

301 GCCATCACCA GCTCCTCCAT CCCCAAGAAC ATCCAGAGCC TCAGGTGCCG CCGCTGTGTG

361 GTCGTGGGGA ACGGGCACCG GCTGCGGAAC AGCTCACTGG AGATGCCAT CAACAAGTAC

421 GATGTGGTCA TCAGATTGAA CAATGCCCCA GTGGCTGGCT ATGAGGGTGA CGTGGGCTCC

481 AAGACCACCA TGCGTCTCTT CTACCCTGAA TCTGCCCACT TCGACCCCAA AGTAGAAAAC

541 AACCCAGACA CACTCCTCGT CCTGGTAGCT TTCAAGGCAA TGGACTTCCA CTGGATTGAG

601 ACCATCCTGA GTGATAAGAA GCGGGTGCGA AAGGGTTTCT GGAAACAGCC TCCCCTCATC

661 TGGGATGTCA ATCCTAAACA GATTCGGATT CTCAACCCCT TCTTCATGGA GATTGCAGCT
```

```
721 GACAAACTGC TGAGCCTGCC AATGCAACAG CCACGGAAGA TTAAGCAGAA GCCCACCACG

781 GGCCTGTTGG CCATCACGCT GGCCCTCCAC CTCTGTGACT TGGTGCACAT TGCCGGCTTT

841 GGCTACCCAG ACGCCTACAA CAAGAAGCAG ACCATTCACT ACTATGAGCA GATCACGCTC

901 AAGTCCATGG CGGGGTCAGG CCATAATGTC TCCCAAGAGG CCCTGGCCAT TAAGCGGATG

961 CTGGAGATGG GAGCTATCAA GAACCTCACG TCCTTCTGA
```

Protein Sequence of ST3GAL4 (SEQ ID NO: 8)
```
  1 MCPAGWKLLA MLALVLVVMV WYSISREDRY IELFYFPIPE KKEPCLQGEA ESKASKLFGN

61 YSRDQPIFLR LEDYFWVKTP SAYELPYGTK GSEDLLLRVL AITSSSIPKN IQSLRCRRCV

121 VVGNGHRLRN SSLGDAINKY DVVIRLNNAP VAGYEGDVGS KTTMRLFYPE SAHFDPKVEN

181 NPDTLLVLVA FKAMDFHWIE TILSDKKRVR KGFWKQPPLI WDVNPKQIRI LNPFFMEIAA

241 DKLLSLPMQQ PRKIKQKPTT GLLAITLALH LCDLVHIAGF GYPDAYNKKQ TIHYYEQITL

301 KSMAGSGHNV SQEALAIKRM LEMGAIKNLT SF
```

Optimised hCG alpha chain

Nucleotide sequence of optimised hCG alpha chain
(SEQ ID NO: 4)
```
  1 GCCCCTGACG TGCAGGACTG CCCCGAGTGC ACCCTGCAGG AAAACCCCTT CTTCAGCCAG

61 CCTGGCGCCC CTATCCTGCA GTGCATGGGC TGCTGCTTCA GCAGAGCCTA CCCCACCCCC

121 CTGCGGAGCA AGAAAACCAT GCTGGTGCAG AAAAACGTGA CCAGCGAGAG CACCTGCTGC

181 GTGGCCAAGA GCTACAACCG GGTGACCGTG ATGGGCGGCT TCAAGGTGGA GAACCACACC

241 GCCTGCCACT GCAGCACCTG CTACTACCAC AAGTCCT
```

Protein sequence of hCG optimised alpha chain (SEQ ID NO: 9)
```
  1 APDVQDCPEC TLQENPFFSQ PGAPILQCMG CCFSRAYPTP LRSKKTMLVQ KNVTSESTCC

61 VAKSYNRVTV MGGFKVENHT ACHCSTCYYH KS
``` hCG alpha polypeptide

Accession number AH007338

Nucleotide sequence of hCG alpha
(SEQ ID NO: 5)
```
  1 ATGGATTACT ACAGAAAATA TGCAGCTATC TTTCTGGTCA CATTGTCGGT GTTTCTGCAT

61 GTTCTCCATT CCGCTCCTGA TGTGCAGGAT TGCCCAGAAT GCACGCTACA GGAAAACCCA

121 TTCTTCTCCC AGCCGGGTGC CCCAATACTT CAGTGCATGG GCTGCTGCTT CTCTAGAGCA

181 TATCCCACTC CACTAAGGTC CAAGAAGACG ATGTTGGTCC AAAAGAACGT CACCTCAGAG

241 TCCACTTGCT GTGTAGCTAA ATCATATAAC AGGGTCACAG TAATGGGGGG TTTCAAAGTG

301 GAGAACCACA CGGCGTGCCA CTGCAGTACT TGTTATTATC ACAAATCTTA A
```

Protein sequence of hCG alpha (SEQ ID NO: 10)
```
  1 MDYYRKYAAI FLVTLSVFLH VLHSAPDVQD CPECTLQENP FFSQPGAPIL QCMGCCFSRA

61 YPTPLRSKKT MLVQKNVTSE STCCVAKSYN RVTVMGGFKV ENHTACHCST CYYHKS
```

---

The invention claimed is:

1. A polynucleotide sequence comprising an optimized hCG α-chain nucleic acid sequence selected from SEQ ID NO:1 and sequences having at least 97% sequence identity thereto, and SEQ ID NO:4 and sequences having at least 97% sequence identity thereto.

2. The polynucleotide sequence of claim 1, comprising the nucleic acid sequence of SEQ ID NO:1.

3. The polynucleotide sequence of claim 1, comprising a nucleic acid sequence having at least 97% sequence identity to SEQ ID NO:1.

4. The polynucleotide sequence of claim 1, comprising the nucleic acid sequence of SEQ ID NO:4.

5. The polynucleotide sequence of claim 1, comprising a nucleic acid sequence having at least 97% sequence identity to SEQ ID NO:4.

6. A cultured transformed cell having integrated into its genome an optimized hCG α-chain polynucleotide sequence comprising SEQ ID NO:1 or a sequence having at least 96.5% sequence identity thereto or SEQ ID NO:4 or a sequence having at least 96.5% sequence identity thereto.

7. The transformed cell according to claim 6, wherein the integrated sequence comprises SEQ ID NO:1.

8. The transformed cell according to claim 6, wherein the integrated sequence comprises a sequence having at least 96.5% sequence identity to SEQ ID NO:1.

9. The transformed cell according to claim 6, wherein the integrated sequence comprises a sequence having at least 97% sequence identity to SEQ ID NO:1.

10. The transformed cell according to claim 6, wherein the integrated sequence comprises SEQ ID NO:4.

11. The transformed cell according to claim 6, wherein the integrated sequence comprises a sequence having at least 96.5% sequence identity to SEQ ID NO:4.

12. The transformed cell according to claim 6, wherein the integrated sequence comprises a sequence having at least 97% sequence identity to SEQ ID NO:4.

13. The transformed cell according to claim 6, wherein the transformed cell is the PER.C6 cell line deposited under ECACC No. 96022940 transformed to have integrated into its genome the optimized hCG α chain polynucleotide sequence.

14. The transformed cell according to claim 6, further having integrated into its genome a cDNA encoding alpha-2,3-sialyltransferase.

15. The transformed cell according to claim 6, further having integrated into its genome a nucleic acid sequence encoding the hCG β chain.

16. A method for producing recombinant protein in a cell, comprising culturing a cell according to claim 6 in a suitable medium, and harvesting the recombinant protein.

17. A method for producing recombinant hCG in a cell, comprising culturing a cell according to claim 13 in a suitable medium, and harvesting the recombinant protein.

* * * * *